(12) United States Patent
Ono et al.

(10) Patent No.: US 6,802,226 B2
(45) Date of Patent: Oct. 12, 2004

(54) PHYSICAL AMOUNT ESTIMATING APPARATUS, ROAD SURFACE FRICTION CONDITION ESTIMATING APPARATUS, STEERING ANGLE NEUTRAL POINT ESTIMATING APPARATUS AND AIR PRESSURE REDUCTION ESTIMATING APPARATUS

(75) Inventors: Eiichi Ono, Aichi-ken (JP); Yoshitoshi Watanabe, Aichi-ken (JP); Masanori Miyashita, Aichi-ken (JP); Yuji Muragishi, Aichi-ken (JP); Katsuhiro Asano, Aichi-ken (JP)

(73) Assignee: Kabushiki Kaisha Toyota Chuo Kenkyusho, Aichi-gun (JP)

( * ) Notice: Subject to any disclaimer, the term of this patent is extended or adjusted under 35 U.S.C. 154(b) by 203 days.

(21) Appl. No.: 10/193,220

(22) Filed: Jul. 12, 2002

(65) Prior Publication Data

US 2003/0051560 A1 Mar. 20, 2003

(30) Foreign Application Priority Data

Jul. 12, 2001 (JP) .................................. 2001-212683
Jun. 24, 2002 (JP) .................................. 2002-183413

(51) Int. Cl.[7] .............................................. G01L 3/02
(52) U.S. Cl. .............................................. 73/862.325
(58) Field of Search .................. 73/862.08, 862.325, 73/862.193

(56) References Cited

U.S. PATENT DOCUMENTS

| | | | |
|---|---|---|---|
| 5,182,711 A | * | 1/1993 | Takahashi et al. ............ 701/41 |
| 5,698,956 A | * | 12/1997 | Nishino et al. ............. 318/432 |
| 6,407,524 B1 | * | 6/2002 | Endo et al. ................. 318/432 |
| 6,644,433 B2 | * | 11/2003 | Sato .......................... 180/446 |

FOREIGN PATENT DOCUMENTS

| | | |
|---|---|---|
| DE | 39 23 654 | 2/1990 |
| DE | 38 42 334 | 6/1990 |
| EP | 0 718 174 | 6/1996 |
| JP | 6-221968 | 8/1994 |
| JP | 11-59466 | 3/1999 |
| JP | 11-287749 | 10/1999 |
| WO | WO 01/60682 | 8/2001 |

* cited by examiner

*Primary Examiner*—Max Noori
(74) *Attorney, Agent, or Firm*—Oblon, Spivak, McClelland, Maier & Neustadt, P.C.

(57) ABSTRACT

A physical amount estimating apparatus including first outputting means for outputting a first physical amount that does not include a hysteresis characteristic, second outputting means for outputting a second physical amount that has a predetermined physical relationship to the first physical amount and includes a hysteresis characteristic, hysteresis removing means for calculating a corrected value with the hysteresis characteristic removed therefrom based on the second physical amount, and estimating means for estimating a third physical amount based on a physical relationship between the first physical amount and the corrected value.

22 Claims, 23 Drawing Sheets

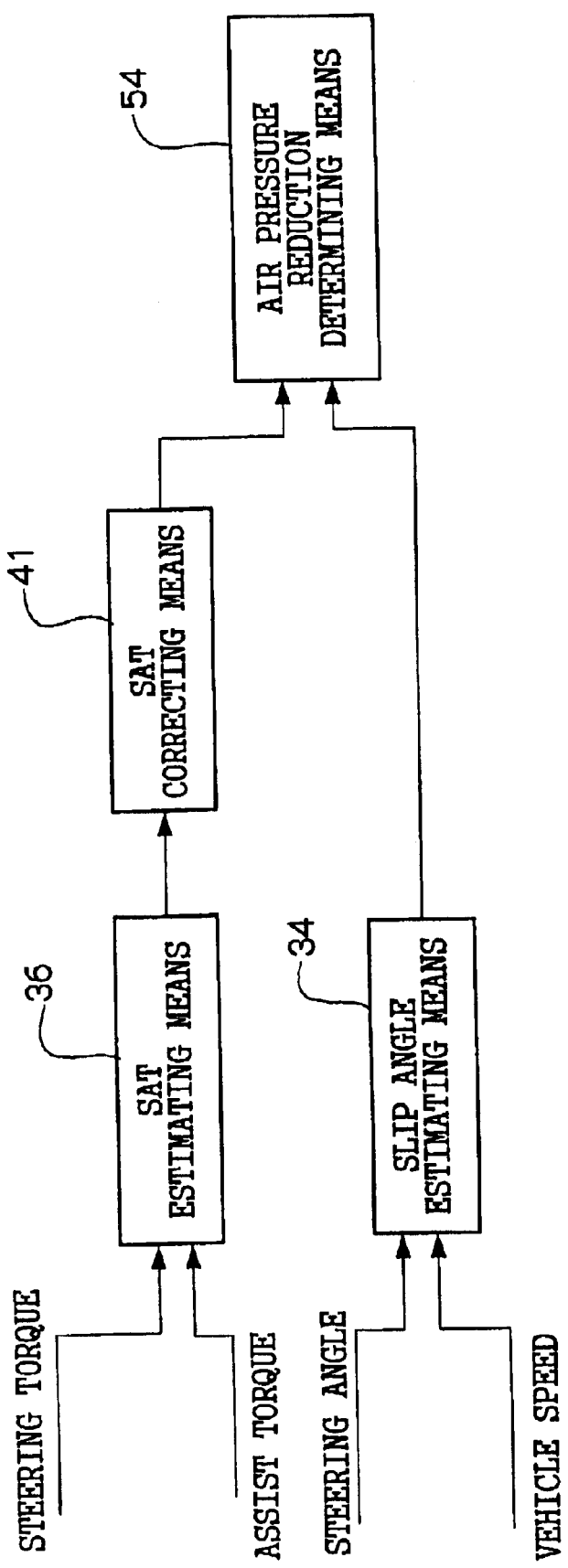

PHYSICAL AMOUNT ESTIMATING APPARATUS, ROAD SURFACE FRICTION CONDITION ESTIMATING APPARATUS, STEERING ANGLE NEUTRAL POINT ESTIMATING APPARATUS AND AIR PRESSURE REDUCTION ESTIMATING APPARATUS

BACKGROUND OF THE INVENTION

1. Field of the Invention

The present invention relates to a physical amount estimating apparatus, a road surface friction condition estimating apparatus, a steering angle neutral point estimating apparatus and a tire air pressure reduction estimating apparatus, and particularly to a physical amount estimating apparatus for estimating a physical amount based on a corrected value with a hysteresis characteristic removed therefrom, a road surface friction condition estimating apparatus for calculating a corrected value with a hysteresis characteristic, caused by influence from viscous friction of Coulomb friction, removed therefrom, using an estimated value of self aligning torque (SAT) and estimating a road surface friction condition based on the calculated corrected value, a steering angle neutral point estimating apparatus for estimating a neutral point of a steering angle based on a corrected value with a hysteresis characteristic removed therefrom and a steering angle, and an air pressure reduction estimating apparatus of a tire for estimating a reduction in air pressure of a tire based on a corrected value with a hysteresis characteristic removed therefrom and an SAT reference value.

2. Description of the Related Art

Japanese Patent Application Laid-open (JP-A) No. 11-287749 discloses technology for detecting a steering angle and steering torque of a tire, calculating a characteristic of the steering torque with regard to the steering angle and calculating a friction coefficient $\mu$ (road surface $\mu$) of a road surface on which a tire is grounded.

According to the related art, the road surface $\mu$, which constitutes a physical amount in correspondence with a grip state, is calculated as an amount of change of the steering torque with regard to an amount of change of the steering angle, and therefore the resulting estimating method is liable to be affected by noise. That is, calculation of an amount of change signifies carrying out differentiation, which amplifies noise, and therefore the estimated value becomes a value that includes a large amount of noise.

Further, according to the related art, the road surface $\mu$ is estimated only when the steering angle is increased in order to steer. Thus, at a maximum steering angle, at which a load applied to the tire is maximized, the steering angle cannot be increased in order to steer, and therefore the friction coefficient cannot be estimated. Inherently, if the road surface $\mu$ is estimated when the load applied to the tire is maximized, that is, near a limit, or in other words, when limit road surface $\mu$ is estimated, accuracy of the estimation is promoted. According to the related art, however, there is a problem in that the road surface $\mu$ cannot be estimated at the maximum steering angle and the road surface $\mu$ can be estimated only before reaching the maximum steering angle.

Meanwhile, a hysteresis characteristic is caused by twisting of a tire tread, Coulomb friction in a power steering apparatus, or the like, between SAT and a slip angle or a steering angle. Therefore, the characteristic differs when increasing the steering angle and when decreasing the steering angle, and according to the related art, in which attention is paid to a change in SAT with regard to a change in the slip angle or the steering angle, a dispersion in the estimated value is caused.

Further, when a driver reduces steering torque to the point of not moving the steering wheel when steering is maintained, although there is no change in the slip angle or the steering angle, as a result of reducing SAT, there is a possibility of erroneously determining that a "reduction in grip" has occurred. That is, according to the above-described related art, although such an erroneous determination is avoided and the dispersion in the estimated value is reduced by carrying out the estimation only when the steering angle is increased, as a result, there is a problem in that a road surface friction condition of the grip state or the like cannot be estimated when decreasing or maintaining the steering angle.

Further, that the road surface friction condition cannot be estimated when decreasing or maintaining the steering angle, signifies that when the tire shifts from a low $\mu$ road to a high $\mu$ road while maintaining the steering angle, or when the grip state is changed by shifting from a high $\mu$ road to a low $\mu$ road, at the time of the change, the road surface friction condition and the grip state cannot be estimated until the steering angle is subsequently increased. Therefore, the estimated value of the grip state according to the related art cannot be utilized as a control parameter for switching a characteristic of a power steering apparatus or ABS, which require swift adaptability in accordance with the grip state.

Further, JP-A Nos. 11-334634 and 11-59466, disclose technology in which reference steering torque, which is set based on a steering angle and vehicle speed, is compared with steering torque, and when a state in which the steering torque is greater than the reference steering torque continues for a certain period of time, it is determined that a reduction in air pressure of a tire has occurred.

In the above-described related art, the steering torque, which includes friction of a steering system, is utilized, and therefore there is a problem in that a change in the steering torque with regard to air pressure is influenced by the friction. As a result, the change cannot accurately be detected and a reduction in air pressure cannot be estimated with high accuracy due to the influence of the friction.

Further, the relationship between the steering angle and the steering torque is also influenced by movement of the vehicle, which is a dynamic characteristic, aside from the friction of the steering system. Therefore, there is a concern that the accuracy of estimation is deteriorated when fast steering is carried out.

As a countermeasure against the above-described problem, according to the related art, a condition is added that the state in which the steering torque is greater than the reference steering torque must continue for a certain period of time or longer, and due to the condition, the problem of deterioration in accuracy is alleviated. As a result of the condition, however, chances to carry out estimation are decreased, and there is a new problem in that estimation time is delayed.

SUMMARY OF THE INVENTION

The invention has been carried out in order to resolve the above-described problem and it is an object thereof to provide a physical amount estimating apparatus capable of estimating a highly accurate physical amount by removing a hysteresis characteristic such that a dispersion is not caused in an estimated value, a road surface friction condition estimating apparatus capable of accurately estimating a road surface friction condition without steering to increase a steering angle, a steering angle neutral point estimating apparatus capable of accurately estimating a neutral point of a steering angle and an air pressure reduction estimating apparatus of tire capable of estimating reduction in the pressure of tire.

In order to achieve the above-described object, a physical amount estimating apparatus of the invention is constituted by including first outputting means for outputting a first physical amount which is not provided with a hysteresis characteristic, second outputting means for outputting a second physical amount which has a predetermined physical relationship with the first physical amount and has a hysteresis characteristic, hysteresis removing means for calculating a corrected value removed of the hysteresis characteristic based on the second physical amount, and estimating means for estimating a third physical amount based on a physical relationship between the first physical amount and the corrected value.

According to the invention, the hysteresis characteristic is removed based on the physical amount having the predetermined physical relationship with the first physical amount which is not provided with the hysteresis characteristic and having the hysteresis characteristic, other physical amount is estimated based on the physical amount removed of the hysteresis characteristic and therefore, the highly accurate physical amount can be estimated. Thereby, still other physical amount can be estimated from the highly accurate physical amount and therefore, the dispersion is not caused in the estimated physical amount.

According to the invention, it is possible that the first physical amount is constituted by a physical amount with regard to a steering state of a steered wheel, for example, either one of a slip angle of the steered wheel and a side force of the steered wheel, the second physical amount is constituted by an estimated value of a self aligning torque estimated from a steering torque and an assist torque, the corrected value is constituted by a corrected value of the self aligning torque calculated from the estimated value of the self aligning torque and the third physical amount is constituted by a physical amount with regard to either one of a wheel state in running a vehicle and a road state.

It is possible that the corrected value of the self aligning torque is calculated by a calculating equations, which each include a gradient represented by a ratio of a change in the corrected value of the self aligning torque to a change in the estimated value of the self aligning torque, and which equations are different for respective regions due to a gradient in a region, where the estimated value of the self aligning torque varies due to Coulomb friction, being made smaller than gradients of regions other than the region.

Further, the hysteresis characteristic can be removed by representing a predetermined physical relationship between the physical amount having the hysteresis characteristic and the above-described same physical amount which is not provided with the hysteresis characteristic by a graph, a table or the like and converting the physical amount having the hysteresis characteristic into the physical amount which is not provided with the hysteresis characteristic based on the physical relationship. In this case, conversion is facilitated by previously determining an initial value in accordance with previous history.

The physical amount with regard to either of the wheel state in running the vehicle and the road state (for example, air pressure reduction of tire, or road surface friction condition) can be estimated based on either one of the slip angle of the steered wheel and the side force of the steered wheel and the corrected value of the self aligning torque, or based on a reference value of the self aligning torque set in accordance with either one of the slip angle of the steered wheel and the side force of the steered wheel, and the corrected value of the self aligning torque.

Further, the physical amount with regard to either one of the wheel state in running the vehicle and the road state can be estimated also based on a gradient of the corrected value of the self aligning torque represented by the ratio of the change of the corrected value of the self aligning torque to the change of the slip angle, the gradient of the corrected value of the self aligning torque represented by the ratio of the change of the corrected value of the self aligning torque to the change of the side force.

Further, the physical amount with regard to either one of the wheel state in running the vehicle and the road state can also be estimated based on the physical amount with regard to a steering state of a steered wheel and either one of a reference value of the slip angle and the corrected value of the self aligning torque.

The reference value of the slip angle may be calculated by a calculating equations, which each include a gradient represented by a ratio of a change in the reference value of the slip angle to a change in the estimated value of the self aligning torque, and which equations are different for respective regions due to a gradient in a region, where the estimated value of the self aligning torque varies due to Coulomb friction, being made smaller than gradients of regions other than the region.

A road surface friction condition estimating apparatus according to the invention is constituted by including a steering angle sensor for detecting a steering angle, a vehicle speed sensor for detecting a vehicle speed, a torque sensor for detecting a steering torque, an assist torque sensor for detecting an assist torque of steering, slip angle estimating means for estimating a slip angle of a steered wheel based on the steering angle and the vehicle speed, self aligning torque estimating means for estimating a self aligning torque based on the steering torque and the assist torque, hysteresis removing means for calculating a corrected value removed of a hysteresis characteristic based on an estimated value of the self aligning torque, and friction state estimating means for estimating a road surface friction condition from the corrected value and the slip angle.

The slip angle estimating means of the road surface friction condition estimating apparatus of the invention, estimates the slip angle of the steered wheel (for example, front wheel) by using the steering angle and the vehicle speed based on a vehicle motion model. The self aligning torque (SAT) estimating means estimates SAT constituting road reaction force based on the steering torque and the assist torque, specifically by adding the steering torque and the assist torque. The steering torque is detected by, for example, a torque sensor attached coaxially with a steering wheel and the assist torque is calculated, for example, from current of the electric power steering apparatus.

Further, accuracy of estimating SAT can be promoted also by subtracting viscous friction torque produced in proportion to steering angular velocity from a value added with the steering torque and the assist torque. Further, SAT may be estimated by a method of a disturbance observer described in Japanese Patent Application No. 2000-370704 by utilizing also the steering angular velocity other than the steering angle. By using the method of the disturbance observer, there can be estimated SAT in consideration of a torque produced by inertia of the power steering apparatus.

The hysteresis removing means outputs the corrected value removed of the hysteresis characteristic based on the estimated value of the self aligning torque.

That is, the hysteresis removing means can calculate, as the corrected value, the slip angle with regard to the estimated value of the self aligning torque based on the physical relationship between the self aligning torque having the hysteresis characteristic and the slip angle. That is, there is outputted, as the corrected value, the slip angle (slip angle reference value) in consideration of the hysteresis characteristic produced by Coulomb friction of the power steering apparatus from the estimated value of SAT estimated by the SAT estimating means. The reference value of the slip angle is, for example, a slip angle of the steered wheel, for example, front wheel produced in a steering region having a sufficiently high grip state and allowance and therefore, the hysteresis characteristic with regard to the estimated value of the self aligning torque is removed.

The friction state estimating means estimates the grip state, that is, the road surface friction condition by comparing the slip angle of the steered wheel estimated by the slip angle estimating means and the reference value of the slip angle outputted from the hysteresis removing means and utilizing the fact that the more reduced is the grip state, that is, the road surface friction condition, the larger the slip angle becomes than the reference value of the slip angle.

Further, the hysteresis removing means may calculate the self aligning torque removed of the hysteresis characteristic from the estimated value of the self aligning torque as the corrected value of the self aligning torque based on the physical relationship between the estimated value of the self aligning torque and the corrected value of the self aligning torque removed of the hysteresis characteristic in place of the above-described removing method. In this case, the self aligning torque removed of the hysteresis characteristic (corrected value of SAT) can directly be calculated from the estimated value of the self aligning torque.

The friction state estimating means estimates the grip state, that is, the road surface friction condition by comparing the reference value of SAT calculated by multiplying the slip angle of the steered wheel estimated by the slip angle estimating means by a coefficient which is changed in accordance with vehicle speed or kind of tire and the corrected value of SAT and utilizing the fact that the more reduced is the grip state, that is, the road surface friction condition, the smaller the corrected value of SAT becomes than the reference value of SAT.

As has been explained above, according to the invention, there is outputted the corrected value removed of the hysteresis characteristic based on the self aligning torque, the road surface friction condition is estimated based on the corrected value and therefore, road surface friction condition can be estimated accurately in all of a range of the steering angle.

Further, a steering angle neutral point estimating means according to the invention is constituted by including a steering angle sensor for detecting a steering angle, a torque sensor for detecting a steering torque, an assist torque sensor for detecting an assist torque of steering, self aligning torque estimating means for estimating a self aligning torque based on the steering torque and the assist torque, hysteresis removing means for calculating a corrected value removed of the hysteresis characteristic constituting an initial value by a value when an estimated value of the self aligning torque becomes 0 based on the estimated value of the self aligning torque, and neutral point estimating means for estimating the steering angle when the corrected value becomes 0 as a neutral point of the steering angle based on the corrected value and the steering angle.

The self aligning torque (SAT) estimating means according to the invention estimates SAT based on the steering torque and the assist torque as explained above. The hysteresis removing means outputs the corrected value removed of the hysteresis characteristic from the physical relationship between SAT having the hysteresis characteristic and SAT removed of the hysteresis characteristic by constituting an initial value by a value when the estimated value of SAT become 0. Further, the neutral point estimating means estimates the steering angle when the corrected value becomes 0 as the neutral point of the steering angle based on the corrected value and the steering angle.

An air pressure reduction estimating apparatus of tire according to the invention is constituted by including a steering angle sensor for detecting a steering angle, a vehicle speed sensor for detecting a vehicle speed, a torque sensor for detecting a steering torque, an assist torque sensor for detecting an assist torque of steering, slip angle estimating means for estimating a slip angle of a steered wheel based on the steering angle and the vehicle speed, self aligning torque estimating means for estimating a self aligning torque based on the steering torque and the assist torque, hysteresis removing means for calculating a corrected value of the self aligning torque removed of a hysteresis characteristic based on an estimated value of the self aligning torque, and air pressure reduction estimating means for estimating whether an air pressure of a tire is reduced based on the corrected value of the self aligning torque and the slip angle.

According to the air pressure reduction estimating apparatus of tire, there may be estimated whether the air pressure of tire is reduced by providing a lateral acceleration sensor for detecting lateral acceleration and a yaw angular velocity sensor for detecting yaw angular velocity in place of the steering angle sensor and the vehicle speed sensor, for estimating a side force of the steered wheel based on the lateral acceleration and the yaw angular velocity and based on the corrected value of the self aligning torque and the side force.

The reduction in the air pressure of tire can be estimated based on the corrected value of the self aligning torque and a reference value of the self aligning torque set in accordance with the slip angle of the steered wheel, based on the corrected value of the self aligning torque and the reference value of the self aligning torque set in accordance with the side force of the steered wheel, or based on a gradient of the corrected value of the self aligning torque represented by a ratio of a change of the corrected value of the self aligning torque to a change of the slip angle.

Further, it may be estimated whether the air pressure of tire is reduced based on a gradient of the corrected value of the self aligning torque represented by a ratio of a change of the corrected value of the self aligning torque to the change of the side force.

The ratio of the reference value of SAT to the corrected value of SAT calculated by the air pressure reduction determining means, is a value which is increased when the air pressure is reduced and determination of air pressure reduction can be carried out when the value exceeds a threshold. However, the value is simultaneously a value representing the grip state and becomes a small value when the grip is reduced as in running on the low $\mu$ road. Therefore, when the ratio of the reference value of SAT to the corrected value of SAT exceeds the threshold of determining the air pressure reduction, it can be determined that the air pressure is reduced and when the ratio of the reference value of SAT to the corrected value of SAT becomes lower than the threshold of determining reduction of the grip, it can be determined that the grip is reduced.

Further, whereas the reduction of the ratio of the reference value of SAT to the corrected value of SAT caused by the reduction of grip is brought about in accordance with steering and the change is comparatively fast, the increase of the ratio of the reference value of SAT to the corrected value of SAT caused by air pressure reduction, is slow in the change. Therefore, when the ratio of the reference value of SAT to the corrected value of SAT is identified by an on-line least squares method, in contrast to a logic for estimating the grip degree, according to a logic of estimating air pressure, it is preferable that the slow change of the ratio of the reference value of SAT to the corrected value of SAT is caught by setting a large forgetting factor or thinning data referred to as decimation. Further, when air pressure reduction is determined, it is preferable to use data at a vicinity of a straight advancement state having the small slip angle and not influenced by the reduction of grip and therefore, it is also conceivable to remove, by selection, data in carrying out comparatively large steering having large slip angle.

As has been explained above, according to the invention, the hysteresis characteristic is removed from the second physical amount having the hysteresis characteristic, the third physical amount is estimated based on the second physical amount removed of the hysteresis characteristic and therefore, there is achieved an effect of capable of estimating the highly accurate physical amount.

Further, the corrected value removed of the hysteresis characteristic is outputted based on the self aligning torque, the road surface friction condition or air pressure reduction of tire is estimated based on the corrected value and therefore, there is achieved an effect of capable of estimating the road surface friction condition or air pressure reduction of tire accurately in all the range of the steering angle.

Further, the corrected value removed of the hysteresis characteristic is outputted based on the self aligning torque, the steering angle neutral point is estimated based on the corrected value and therefore, there is achieved and effect of capable of accurately estimating the steering angle neutral point.

BRIEF DESCRIPTION OF THE DRAWINGS

FIG. 26 is a block diagram showing a fifth embodiment of the invention applied to an apparatus for estimating a reduction in air pressure of a tire.

DETAILED DESCRIPTION OF THE PREFERRED EMBODIMENTS

A first embodiment of the present invention, applied to a vehicle with front-wheel steering, will now be described in detail with reference to the drawings. First, an explanation will be given of a road surface friction condition estimating apparatus according to the first embodiment.

Figure 1:
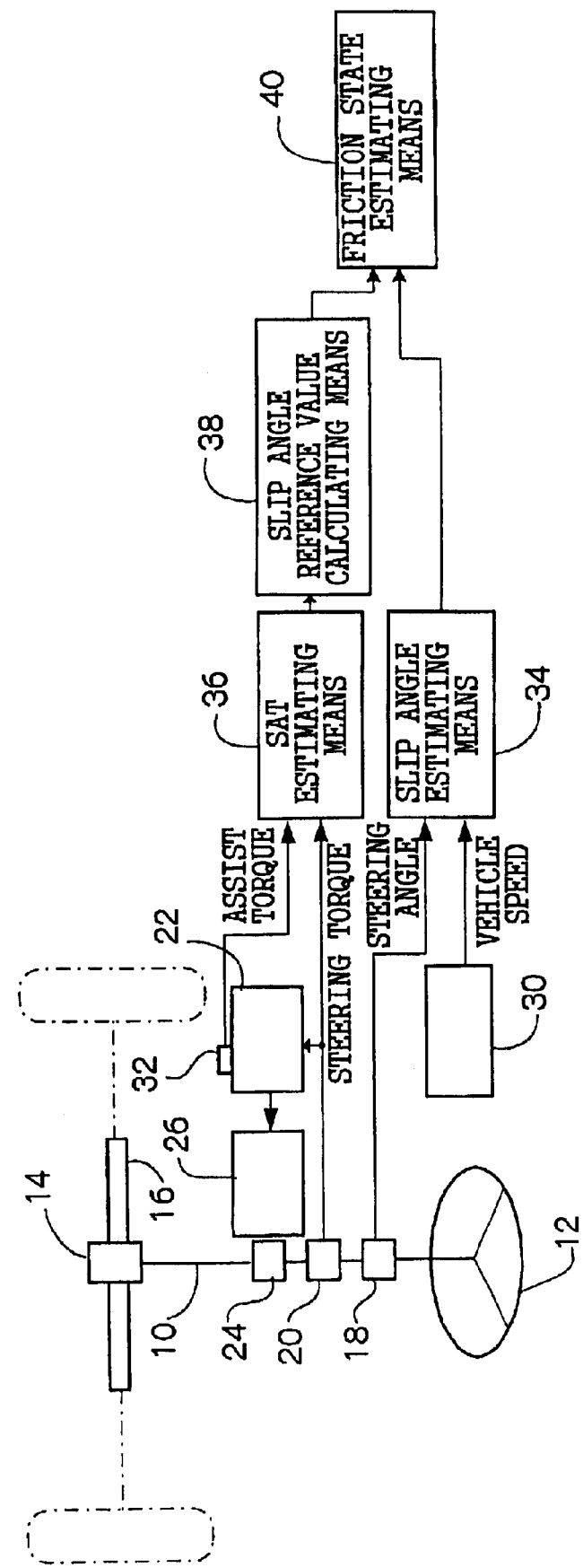
FIG. 1 is a block diagram showing a first embodiment of the present invention applied to a vehicle mounted with an electric power steering apparatus.

As shown in FIG. 1, an electric power steering apparatus mounted to a vehicle is provided with a steering wheel 12 fixed to an upper end portion of a steering shaft 10. A lower end portion of the steering shaft 10 is connected to a steering gear 14 of a rack and pinion type.

Both side portions of a rack of the steering gear 14 are each connected with tie rods 16, and tires are each connected to front end portions of the respective tie rods 16 via a suspension mechanism.

Further, a steering angle sensor 18 for detecting a steering angle and a torque sensor 20 for detecting steering torque are attached to the steering shaft 10, coaxially with the steering shaft. The steering angle sensor 18 outputs a steering angle signal by detecting the steering angle produced by rotating the steering wheel 12. Further, the torque sensor 20 detects rotational torque produced at the steering shaft 10 due to rotation of the steering wheel 12 by a driver, and outputs a steering torque signal in accordance with a direction in which the steering wheel 12 is rotated.

The steering angle torque signal outputted from the torque sensor 20 is inputted to an electric control apparatus 22, which includes a computer for the power steering apparatus and a motor drive circuit.

A speed reducing device 24, including a pair of straight bevel gears or the like, is attached to the steering shaft 10 below a position where the torque sensor 20 is attached. The speed reducing device 24 is connected to a rotating shaft of an electric motor 26 controlled by the electric control apparatus 22. Steering power of the steering wheel 12 can be supplemented by driving of the electric motor 26 by the electric control apparatus 22 and by transmitting rotational force of the electric motor to the steering shaft 10 via the speed reducing device 24.

Further, the vehicle is disposed with a vehicle speed sensor 30 for detecting vehicle body speed (vehicle speed), and the electric control apparatus 22 is disposed with an assist torque sensor 32 for detecting power assist torque from current flowing in the electric power steering apparatus and outputting an assist torque signal.

The steering angle sensor 18 and the vehicle speed sensor 30 are connected to slip angle estimating means 34 of a microcomputer that functions as slip angle estimating means, SAT estimating means, slip angle reference value calculating means and friction state estimating means when considered in terms of functional blocks. The slip angle estimating means 34 calculates a slip angle of the front wheel, which functions as a steered wheel, based on the steering angle and the vehicle speed. Further, the steering torque sensor 20 and the assist torque sensor 32 are connected to SAT estimating means 36 for estimating SAT based on the steering torque and the assist torque.

The SAT estimating means 36 is connected to slip angle reference value calculating means 38 for calculating a reference value of a slip angle from estimated SAT.

Further, although according to the above description, the slip angle estimating means 34, the SAT estimating means 36, the slip angle reference value calculating means 38 and friction state estimating means 40 are constituted by a single microcomputer, these may be constituted by separate apparatuses.

Operation of respective means according to the embodiment will now be described. The slip angle estimating means 34 estimates the slip angle of the front wheel by using the following equations of state by utilizing a dynamic characteristic of motion of the vehicle based on the inputted steering angle signal and the inputted vehicle speed signal.

$$\frac{d}{dt}\begin{bmatrix} v \\ r \end{bmatrix} = \left( \begin{bmatrix} 0 & -1 \\ 0 & 0 \end{bmatrix} u + \begin{bmatrix} -\frac{c_f + c_r}{M} & -\frac{L_f c_f - L_r c_r}{M} \\ -\frac{L_f c_f - L_r c_r}{I_z} & -\frac{L_f^2 c_f + L_r^2 c_r}{I_z} \end{bmatrix} / u \right) \quad (1)$$

$$\begin{bmatrix} v \\ r \end{bmatrix} + \begin{bmatrix} \frac{c_f}{M g_h} \\ \frac{L_f c_f}{I_z g_h} \end{bmatrix} \theta_p$$

$$\hat{\alpha}_f = \begin{bmatrix} 1 & L_f \end{bmatrix} / u \begin{bmatrix} v \\ r \end{bmatrix} - \frac{\theta_p}{g_h} \quad (2)$$

In equation (1), v: lateral velocity (m/s), r: yaw angular velocity (rad/s), $\alpha_f$: front wheel slip angle (rad), u: vehicle speed (m/s), $c_f$: front wheel cornering power (N/rad), $c_r$: rear wheel cornering power (N/rad), $L_f$: front shaft gravitational center distance (m), $L_r$: rear shaft gravitational center distance (m), M: vehicle mass (kg), $I_z$: yaw inertia (kgm$^2$)

$g_h$: gear ratio between steering wheel and actual steering $\theta_p$: steering wheel angle (steering angle)

and the notation ^ indicates an estimated value.

When equations (1) and (2) are made discrete by sampling time τ and represented as functions of vehicle speed, equations (3) and (4) are provided as follows.

$$x(k+1) = \left( \begin{bmatrix} 1 & 0 \\ 0 & 1 \end{bmatrix} + \begin{bmatrix} 0 & -\tau \\ 0 & 0 \end{bmatrix} u(k) + \tau A_s / u(k) \right) x(k) + \tau B_s \theta_p(k) \quad (3)$$

$$\alpha_f(k) = \lfloor 1 \quad L_f \rfloor x(k)/u(k) - \theta_p(k)/g_h \quad (4)$$

$A_s$ and $B_s$ in equation (3) are shown below.

$$A_s = \begin{bmatrix} -\dfrac{c_f + c_r}{M} & -\dfrac{L_f c_f - L_r c_r}{M} \\ -\dfrac{L_f c_f - L_r c_r}{I_z} & -\dfrac{L_f^2 c_f + L_r^2 c_r}{I_z} \end{bmatrix}, B_s = \begin{bmatrix} \dfrac{c_f}{M g_h} \\ \dfrac{L_f c_f}{I_z g_h} \end{bmatrix}$$

Therefore, the front wheel slip angle $\alpha_f$ can be calculated by the above-shown equation (4) for every sampling time $\tau$.

The SAT estimating means 36 estimates an SAT estimated value $T_{SAT}$ constituting road reaction force based on the following equation by adding the steering torque (measured value of torque sensor) $T_p$, measured by the torque sensor 20 attached coaxially with the steering handle, and the assist torque $T_a$ calculated from motor current $I_m$ of the electric power steering apparatus.

$$T_{SAT} = T_p + T_a \quad (5)$$
$$= T_p + \frac{g_p}{g_b} k_m I_m$$

In equation (5), $g_p$ indicates pinion lead, $g_b$ indicates ball screw lead, and $k_m$ indicates assist motor torque constant, all of which are constants.

Further, when viscous friction of the power steering apparatus is taken into account and calculated based on the following equation by using steering speed, the SAT estimated value $T_{SAT}$ can be estimated with further accuracy.

$$T_{SAT} = T_p + \frac{g_p}{g_b} k_m I_m - c\dot{\theta}_p \quad (6)$$

In equation (6), c is a value produced by converting viscosities of respective elements of a motor, a pinion shaft and a rack of the power steering apparatus equivalently into viscosity of the pinion shaft (steering wheel shaft).

Further, by using a disturbance observer, the SAT estimated value $T_{SAT}$ can be estimated, also taking inertia of the power steering apparatus into consideration. Estimation using the disturbance observer will now be described. The dynamic characteristic of the electric power steering apparatus is described by the following differential equation.

$$\left\{ \left(\frac{g_p}{2\pi}\right)^2 M_r + \left(\frac{g_p}{g_b}\right)^2 J_m \right\} \ddot{\theta}_p + c\dot{\theta}_p = T_p + \frac{g_p}{g_b} k_m I_m - T_{SAT} \quad (7)$$

In equation (7), $M_r$ indicates rack mass and $J_m$ indicates motor inertia. Here, when the right hand side of equation (7) is regarded as disturbance estimated by the disturbance observer, the disturbance observer as shown by the following equation can be constituted.

$$\frac{d}{dt}\begin{bmatrix} \hat{\dot{\theta}}_p \\ \hat{\theta}_p \\ \hat{d} \end{bmatrix} = \left( \begin{bmatrix} -c/J_e & 0 & 1/J_e \\ 1 & 0 & 0 \\ 0 & 0 & 0 \end{bmatrix} - G \begin{bmatrix} 1 & 0 & 0 \\ 0 & 1 & 0 \end{bmatrix} \right) \begin{bmatrix} \hat{\dot{\theta}}_p \\ \hat{\theta}_p \\ \hat{d} \end{bmatrix} + G \begin{bmatrix} \dot{\theta}_p \\ \theta_p \end{bmatrix} \quad (8)$$

In equation (8), $$J_e = \left(\frac{g_p}{2\pi}\right)^2 M_r + \left(\frac{g_p}{g_b}\right)^2 J_m \quad (9)$$

$$d = T_p + \frac{g_p}{g_b} k_m I_m - T_{SAT} \quad (10)$$

and G indicates observer gain and the notation ^ indicates an estimated value of a respective state amount. Equation (8) becomes a recurrent equation for estimating disturbance d from steering velocity $d\theta_p/dt$ and steering angle $\theta_p$ by being made discrete.

$$x(k+1) = Ax(k) + B \begin{bmatrix} \dot{\theta}_p(k) \\ \theta_p(k) \end{bmatrix} \quad (11)$$

$$\hat{d}(k) = Cx(k) + D \begin{bmatrix} \dot{\theta}_p(k) \\ \theta_p(k) \end{bmatrix} \quad (12)$$

In these equations, A, B, C, D indicate system matrices produced by making equation (8) discrete. Further, the estimated value of SAT can be calculated by equation (13), shown below.

$$T_{SAT}(k) = T_p(k) + \frac{g_p}{g_b} T_m(k) - \hat{d}(k) \quad (13)$$

The slip angle reference value calculating means 38 calculates a reference value of slip angle (slip angle reference value) in consideration of a hysteresis characteristic, produced by Coulomb friction or the like of the power steering apparatus, from the estimated value of SAT estimated by the SAT estimating means 36. The slip angle reference value is calculated by a logic explained below. The logic is a calculating equation having a gradient (slope) represented by a ratio of a change in the slip angle reference value to a change in the SAT estimated value for calculating the slip angle reference value using an equation which differs for respective regions so that a gradient $K_1$ of a region, where the SAT estimated value varies due to Coulomb friction, is made smaller than a gradient $K_2$ of a region other than the region.

Figure 2:
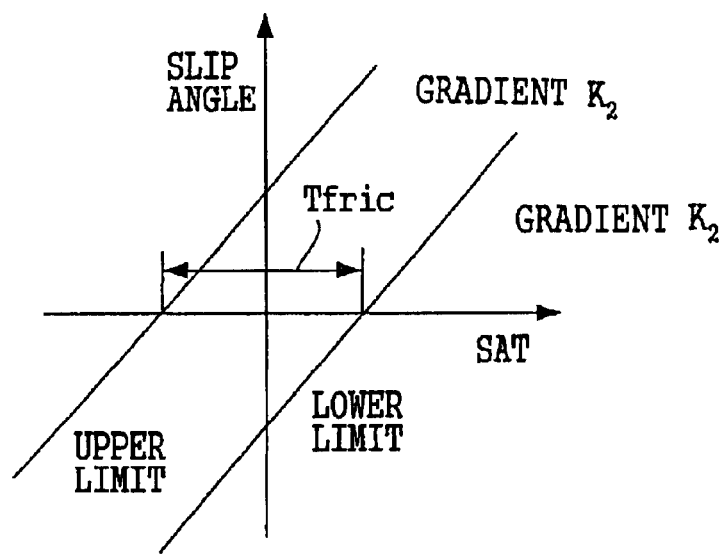
FIG. 2 is a graph showing an upper limit and a lower limit of a slip angle reference value.

FIG. 2 shows an upper limit and a lower limit of the slip angle reference value of a slip angle-SAT model and a gradient of a straight line representing each boundary is indicated by $K_2$. The gradient $K_2$ of the straight line represents a relationship between SAT and the front wheel slip angle produced when steering in a high grip state. A width between the upper limit and the lower limit represents a magnitude of the hysteresis characteristic, and the distance between the two straight lines on the horizontal axis represents friction torque $T_{fric}$ generated by Coulomb friction.

Further, the gradient $K_2$ can estimate the friction state with greater precision by changing the gradient in accordance with vehicle driving speed. Further, it is preferable that $K_2$ is also changed depending on the kind of tire mounted on the vehicle and when kinds of tires, such as studless tires, summer tires or the like, are distinguished, the gradient $K_2$ may be changed in accordance with the kind of tire.

Figure 3:
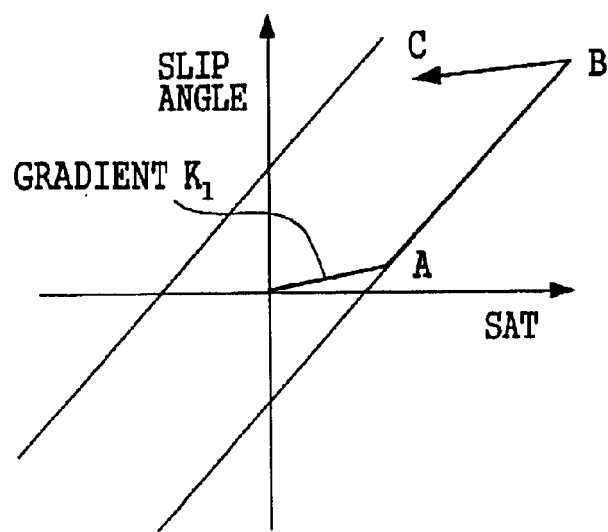
FIG. 3 is a graph for explaining a method for calculating the slip angle reference value.

FIG. 3 shows a method for calculating the slip angle reference value. In a straight driving state, SAT is 0, and 0 is outputted as the slip angle reference value. Next, when steering is carried out and SAT is produced, the slip angle reference value is calculated based on a straight line having a gradient $K_1$ for SAT. In the computer, the slip angle reference value is calculated by the digitized logic, based on the following equation.

$$\alpha_0(k+1)=\alpha_0(k)+K_1\cdot(T_{SAT}(k+1)-T_{SAT}(k)) \quad (14)$$

In equation (14), $\alpha_0$ indicates the slip angle reference value and k indicates time. The gradient $K_1$ is set to be smaller than $K_2$ and represents that even when SAT is varied by Coulomb friction or the like, a produced variation of the slip angle can be reduced. Further, when steering is carried out and a calculated value of the slip angle reference value according to equation (14) reaches point A in FIG. 3 and SAT is increased further, the slip angle reference value is increased in accordance with the following equation along a straight line representing the lower limit of the slip angle—SAT model.

$$\alpha_0(k+1)=\alpha_0(k)+K_2\cdot(T_{SAT}(k+1)-T_{SAT}(k)) \quad (15)$$

Further, when steering is further carried out and point B is reached, increase in steering ceases, and when SAT starts to reduce, the slip angle reference value is reduced by gradient $K_1$ in accordance with equation (14). In the region, a variation in the slip angle reference value is set to be smaller than a variation in SAT. This signifies that even when steering torque of the driver is more or less changed in a state where steering is maintained while turning, the steering angle and the front wheel slip angle are not influenced by Coulomb friction of the power steering apparatus.

Further, when SAT is increased again at point C, reached from point B by reducing SAT, the slip angle reference value is increased toward point B in accordance with equation (14). Further, when SAT is reduced further from point C by steering back and the upper limit of the slip angle—SAT model is reached, the slip angle reference value is reduced along the straight line representing the upper limit in accordance with equation (15). In this way, the hysteresis characteristic shown in FIG. 3 is realized by the equation having two kinds of gradients $K_1$ and $K_2$, which differ depending on the respective regions, and the front wheel slip angle assuming a state having sufficient allowance in the grip state such as the high grip state, i.e., driving on a high $\mu$ road or the like, can be estimated from time-sequential signals of SAT. Therefore, the slip angle reference value calculates the slip angle of the front wheel produced in the steering region having the sufficiently high grip state and allowance from the SAT estimated angle. Further, the slip angle reference value is the slip angle of the front wheel produced in the steering region having the sufficiently high grip state and allowance, and therefore the hysteresis characteristic of the self aligning torque with regard to the estimated value is removed.

The friction state estimating means 40 compares the estimated value of the front wheel slip angle estimated by the slip angle estimating means 34 and the slip angle reference value calculated by the slip angle reference value calculating means and calculates the grip state, i.e., the road surface friction condition, by utilizing the fact that the more the grip state is reduced, the larger the slip angle becomes compared to the slip angle reference value.

Figure 11:
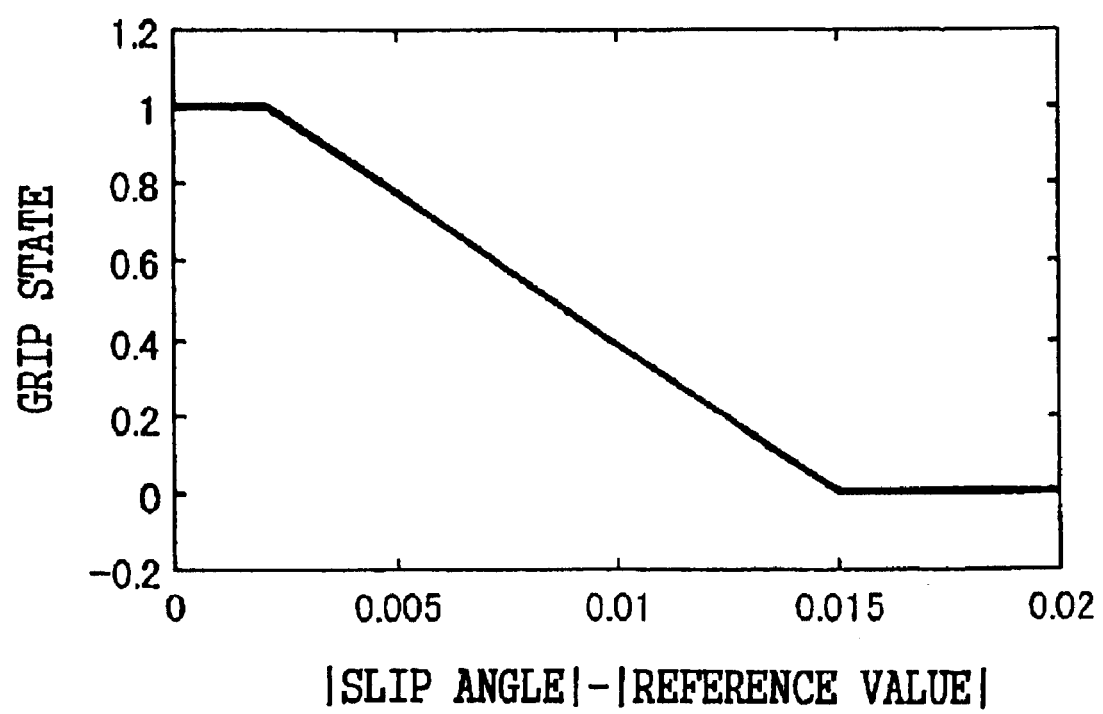
FIG. 11 is a graph showing a relationship between a difference between an absolute value of the slip angle and an absolute value of the reference value of the slip value and a grip state.

The grip state (road surface friction condition) can be calculated from a graph shown in FIG. 11 by using a difference between an absolute value of the front wheel slip angle and an absolute value of the slip angle reference value. The grip state calculated here is normalized in a range of [0,1] showing that the larger the value becomes, the higher the grip becomes. According to the graph shown in FIG. 11, as the difference between the absolute value of the front wheel slip angle and the absolute value of the slip angle reference value becomes larger, the grip state becomes lower, that is, the road surface friction condition is estimated low, and as the difference between the absolute value of the front wheel slip angle and the absolute value of the reference value of the slip angle becomes smaller, the grip state becomes higher, that is, the road surface friction condition is estimated high. Further, in place of the deviation, the road surface friction condition may be estimated by using a ratio of the absolute value of the slip angle reference value to the absolute value of the front wheel slip angle.

Figure 4:
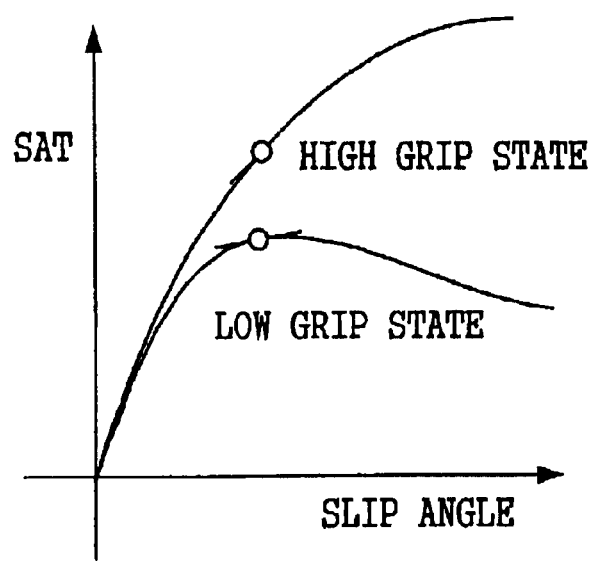
FIG. 4 is a graph showing a difference in an SAT-slip angle characteristic depending on a road surface friction condition.
Figure 5:
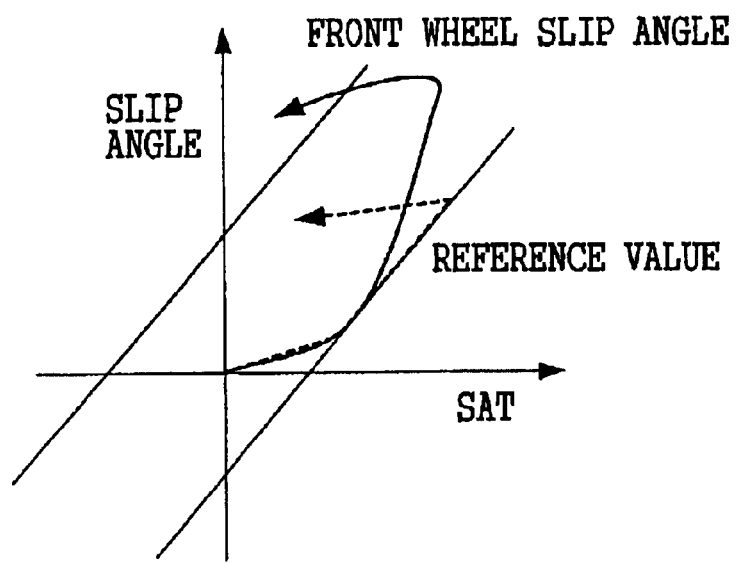
FIG. 5 is a graph showing a slip angle in a low grip state.

Here, when steering is carried out in a state in which the grip state is reduced such as when driving on the low $\mu$ road, as shown in FIG. 4, a gradient, represented by a ratio of a very small change in the SAT estimated value to a very small change in the front wheel slip angle (gradient of a tangential line at a point of a predetermined value of the slip angle—SAT curve), becomes smaller than that in the high grip state. Therefore, when SAT is described in the abscissa and the front wheel slip angle is described in the ordinate, as shown in FIG. 5, in comparison with the slip angle reference value assuming the high grip state, the front wheel slip angle in the low grip state is increased, and the smaller the grip state becomes, the larger the gradient with regard to the front wheel slip angle of SAT becomes. The slip angle reference value calculates the slip angle of the front wheel produced in the steering region having the sufficiently high grip state and allowance from SAT, and therefore by comparing the front wheel slip angle and the slip angle reference value by utilizing the characteristic, reduction of the grip state can be determined. Further, although the deviation between the front wheel slip angle and the slip angle reference value may be utilized as an index of reduction of grip as explained above, weighting may be carried out for the slip angle reference value in accordance with vehicle speed, tire kind, a state of braking or the like, and the value may be normalized for use.

According to this embodiment, by using the model for estimating the slip angle in the high grip state from the time-sequential signals of SAT and comparing the slip angle reference value constituting the output of the model and an actual front wheel slip angle (estimated from steering angle), the grip state is determined. The model takes the hysteresis characteristic into account to constitute a model in which, for example, even when the driver reduces the steering power to a degree that the steering wheel is not moved while maintaining the position of the steering wheel, the slip angle reference value constituting the output of the model is not reduced considerably. Therefore, the grip state can be estimated by comparing the slip angle reference value and the estimated value of the front wheel slip angle even in the state, where the position of the steering wheel is maintained, in which the steering power of the driver is varied.

Although according to the first embodiment, similarly as in the related art, the road surface friction condition is estimated by utilizing the physical relationship between SAT and the slip angle, it is conceivable to conversely estimate the road surface friction condition including the grip state by calculating the reference value of SAT from the slip angle, by the slip angle—SAT model, and compare the reference value of SAT and actual SAT (SAT estimated value).

However, as described above, the actual SAT is significantly influenced by variation in the steering force of the driver in a state of maintained steering. Therefore, in a constitution where SAT, which has a large error factor, is compared with the model output, error in estimation is considerable, and estimation in a state of maintained steering becomes difficult, similarly as in the related art.

In contrast thereto, according to the first embodiment, attention is paid to the slip angle, which has a small variation in a state of maintained steering, a comparison is made between the slip angle and the slip angle reference value, and therefore even in a state of maintained steering or when steering back, the road surface friction condition, including the grip state, can accurately be estimated.

Further, being capable of estimating the road surface friction condition when steering back or in a state of maintained steering, signifies that, for example, when the grip state is changed by shifting from a low $\mu$ road to a high $\mu$ road or shifting from a high $\mu$ road to a low $\mu$ road in a state of maintained steering, the road surface friction condition can be estimated at the time of change without causing a delay in estimation. Therefore, a characteristic of a power steering apparatus or ABS, which require swift adaptability that has been impossible in the related art, can also be utilized as a control parameter that switches in accordance with the grip state.

Next, experimental results of estimating the road surface friction condition according to the first embodiment will be explained. As explained above, the slip angle of the front wheel is estimated by the slip angle estimating means 34, utilizing the dynamic characteristic of the motion of the vehicle, based on equations (3) and (4). SAT is estimated by the SAT estimating means 36, based on equation (6), by adding the steering torque, measured by the torque sensor 20, which is attached coaxially with the steering wheel, and the assist torque, calculated using current of the electric power steering apparatus, taking into account the viscous friction of the power steering apparatus, and using the steering speed.

Figure 6:
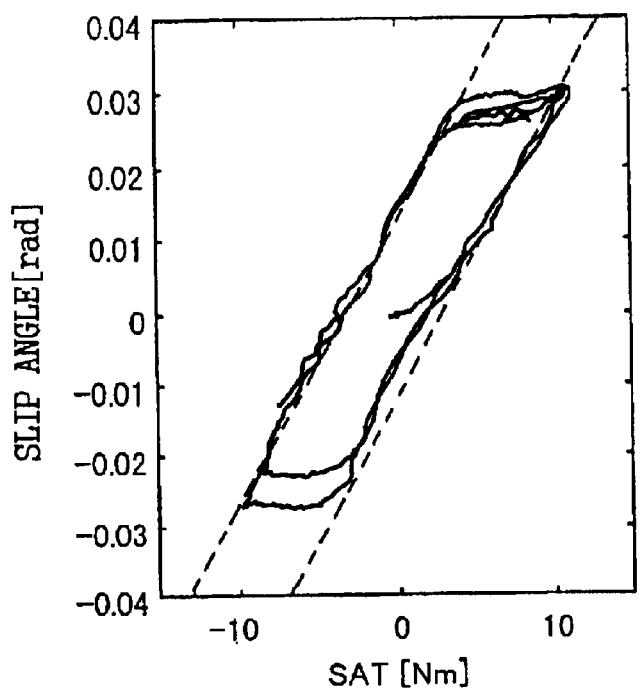
FIG. 6 is a graph showing a relationship between SAT and the slip angle after compensating for viscosity.

FIG. 6 shows a relationship between the front wheel slip angle, calculated by equations (3) and (4), and the SAT estimated value, calculated by equation (6), when steering is carried out while driving on a high $\mu$ road at 30 km/h. FIG. 6 shows straight dotted lines that show upper and lower limits of the slip angle reference value in correspondence with the relationship between SAT and the front wheel slip angle (see FIG. 2) produced when steering is carried out in the high grip state.

Figure 7:
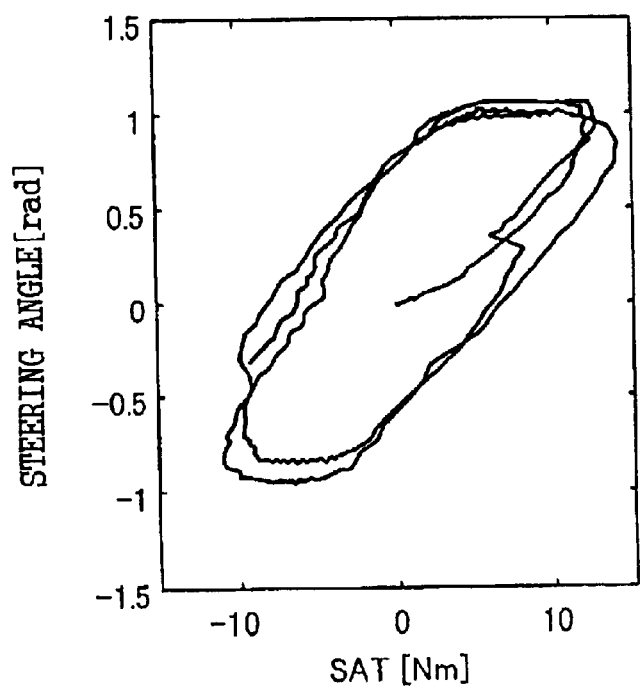
FIG. 7 is a graph showing a relationship between SAT and the slip angle before compensating for viscosity.

Further, FIG. 7 shows a relationship with SAT calculated based on equation (5), without taking the steering angle and the viscosity into consideration, by using the same experimental results. It can be seen that the relationship passes through the broken lines (straight lines showing the upper and lower limits) with excellent reproducibility by using the slip angle constituting a basic state amount of force generated in the tire in place of the steering and taking the viscous friction produced in the power steering apparatus into consideration. The characteristic constitutes a basis of estimating the road surface friction condition including the grip state, and it can be expected that accuracy of estimation is promoted in comparison with that in FIG. 7.

Figures 8A, 8B:
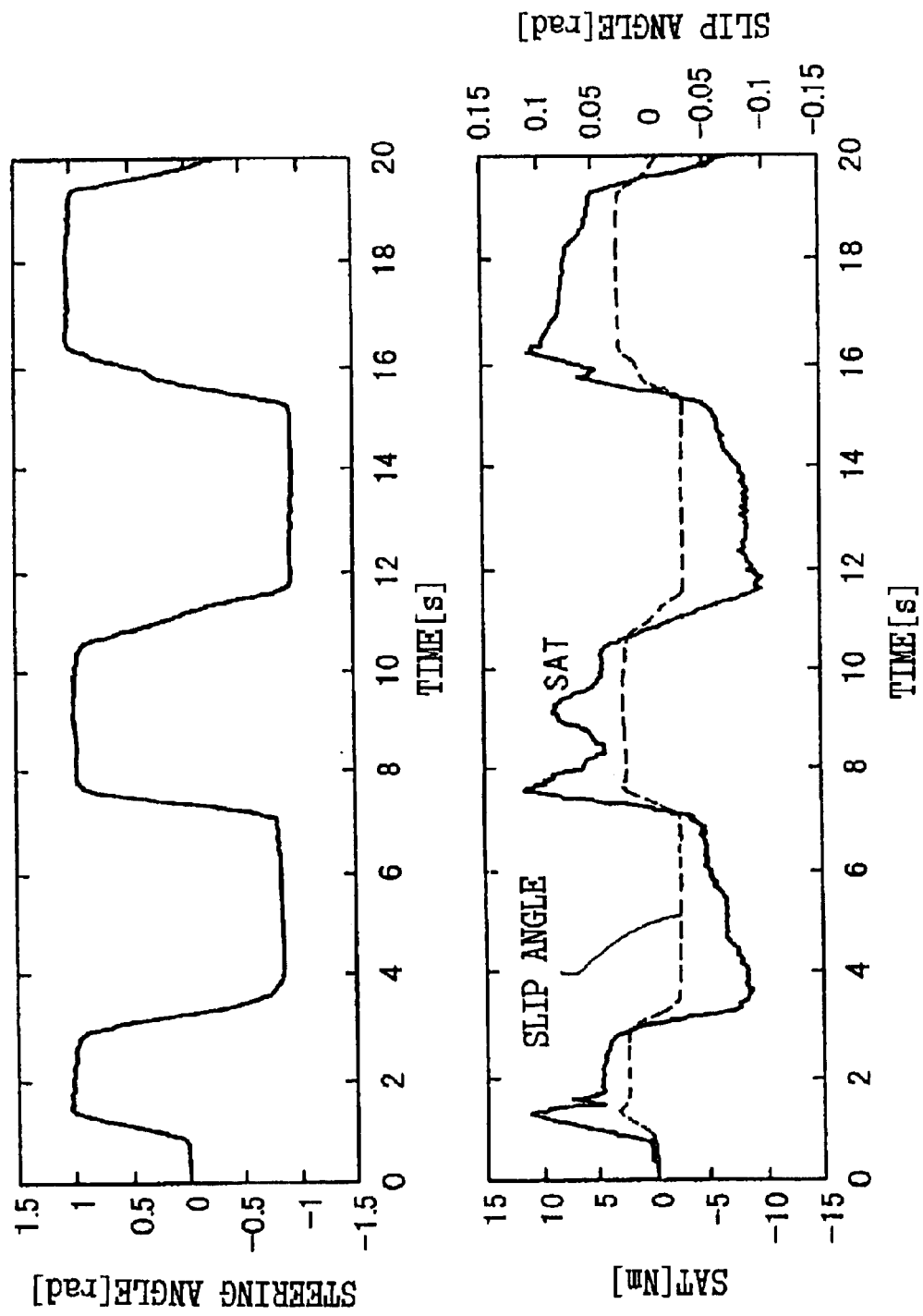
FIG. 8A is a graph showing change, over time, of a steering angle.
FIG. 8B is a graph showing change, over time, of SAT and the slip angle.

Further, FIGS. 8A and 8B show temporal response of the experimental results (SAT is a value compensated for the viscosity). According to the experiment, there is carried out stepped steering of repeating steering and maintaining of steering as shown by FIG. 8A, and the estimated value of the front wheel slip angle at this occasion is constituted by a stepped waveform in accordance with the steering angle. In contrast thereto, as shown in FIG. 8B, SAT is reduced in maintaining steering and reproducibility is not observed in a waveform in reducing SAT. This represents that the steering force of the driver when maintaining steering is varied and according to the method of comparing SAT with the model output, it can be predicted that it is difficult to estimate the accurate grip state due to being influenced by the variation.

In contrast thereto, a waveform of the slip angle in maintaining steering is stabilized and it can be understood that the grip state can accurately be estimated even when maintaining steering according to the embodiment in which the slip angle is compared with the model output (slip angle reference value).

Figure 9:
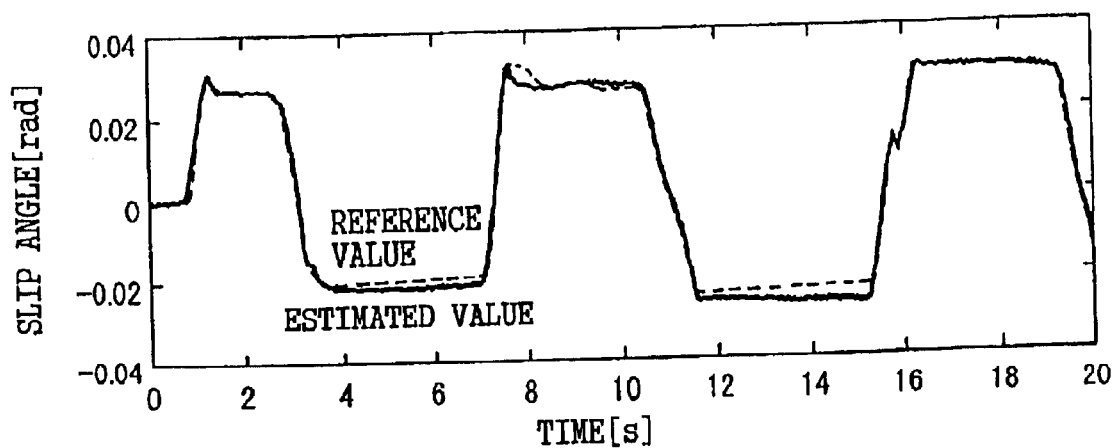
FIG. 9 is a graph showing change, over time, of a reference value of the slip angle and an estimated value of the slip angle when driving on a high $\mu$ road.

According to the slip angle reference value calculating means 38, the reference value of the slip angle is calculated in consideration of the hysteresis characteristic produced by Coulomb friction of the power steering apparatus from the SAT estimated value estimated by the SAT estimating means 36. First, an initial value of the slip angle reference value is set to 0 in a straight driving state in which the steering angle is 0 and SAT becomes 0. Next, when steering is started and SAT is outputted, the slip angle reference value is calculated in accordance with the recurrent equations of equations (14) and (15). Here, the gradient $K_2$ representing the relationship between SAT and the front wheel slip angle, produced when steering under the high grip state, is set to change in accordance with the vehicle speed. FIG. 9 shows a comparison between a result of calculating the slip angle reference value by the above-described algorithm from SAT of FIG. 8B and the front wheel slip angle estimated value. By the algorithm, in consideration of the hysteresis characteristic, the slip angle reference value constituting the output becomes a substantially constant value although the waveform of SAT constituting the input of the model is provided with the characteristic of being reduced or vibrated in maintaining therein. Further, excellent coincidence between the slip angle reference value and the slip angle estimated value is observed on the high $\mu$ road where the experiment is carried out.

Figure 10:
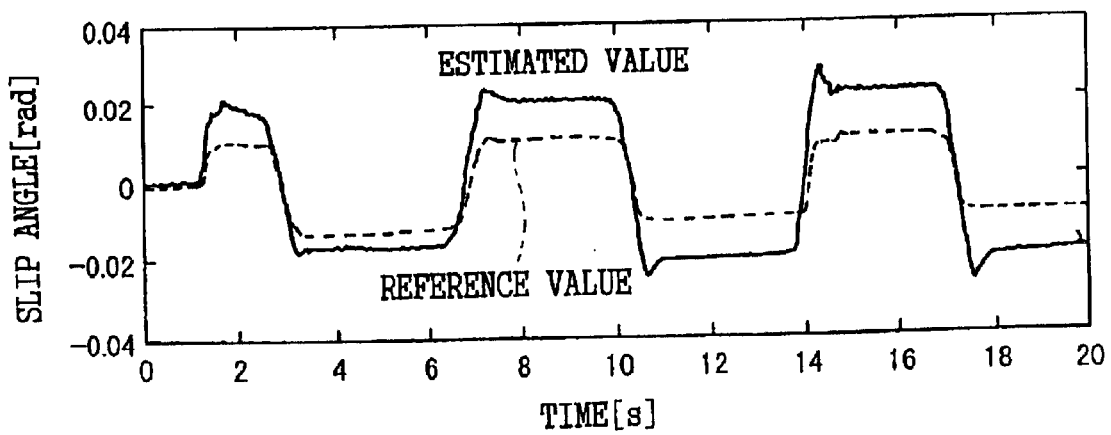
FIG. 10 is a graph showing change, over time, of the reference value of the slip angle and the estimated value of the slip angle when driving on a low $\mu$ road.

FIG. 10 shows results of carrying out an experiment similar to that in FIG. 9 on a low $\mu$ road in which the grip state is lowered. According to the experiment, although steering is carried out at a steering angle substantially similar to that in FIG. 9 and an outputted slip angle estimated value similar to that in FIG. 9 is obtained, it is observed that the reference value of the slip angle calculated from SAT is smaller and a deviation is produced between the estimated value of SAT and the reference value of SAT. This is brought about because, due to a reduction in the grip state, the actual front wheel slip angle is increased in comparison with the slip angle reference value assuming the high grip state.

The grip state is calculated by the friction state estimating means 40 by comparing the front wheel slip angle, estimated by the slip angle estimating means 34, with the slip angle reference value, calculated by the slip angle reference value calculating means 38. The grip state is calculated from the graph shown in FIG. 11 by using the difference between the absolute value of the front wheel slip angle and the absolute value of the slip angle reference value. The grip state calculated here is normalized in the range of [0, 1] showing that the larger the value becomes, the higher the grip becomes. According to the graph shown in FIG. 11, the larger the difference between the absolute value of the front wheel slip angle and the reference value of the slip angle becomes, the lower the grip state, i.e., the road surface friction condition, is estimated, and the smaller the difference between the absolute value of the front wheel slip angle and the absolute value of the slip angle reference value, the higher the grip state, i.e., the road surface friction condition, is estimated.

Figure 12:
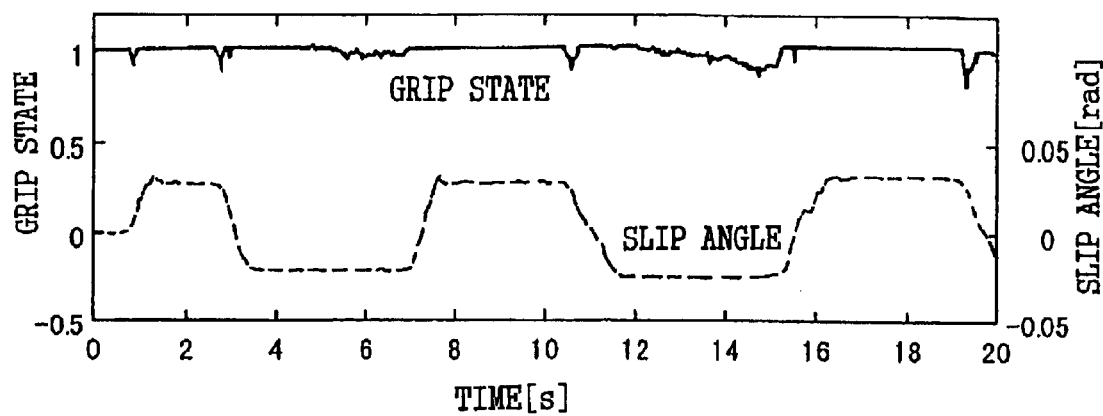
FIG. 12 is a graph showing change, over time, of the grip state and the slip angle when driving on a high $\mu$ road.
Figure 13:
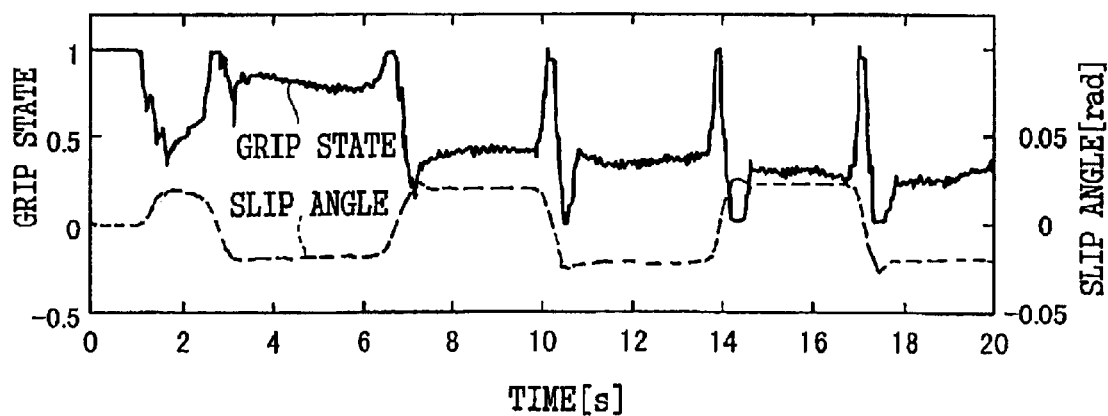
FIG. 13 is a graph showing change, over time, of the grip state and the slip angle when driving on a low $\mu$ road.

FIG. 12 shows the grip state and the slip angle estimated value when driving on the high $\mu$ road. It can be estimated that when running on the high μ road, in the case of such a degree of slip angle, a high grip state is always brought about regardless of presence or absence of the slip angle. FIG. 13 shows a grip state and a slip angle estimated value similar to those in FIG. 12 when driving on the low μ road. It can be understood that the grip state is lowered when driving on the low μ road. Further, it can be understood that there can be accurately estimated a phenomenon in which the grip state becomes 1 at a point at which the slip angle becomes close to 0 when steering, and in which at a region close to straight driving the grip is recovered.

Next, an explanation will be given of estimation of friction torque $T_{fric}$, which causes the hysteresis characteristic produced in the estimated value of SAT. Here, there is calculated a difference between the estimated value of SAT when the absolute value is maximized when increasing steering of the steering wheel and the estimated value of SAT at a point of steering back the steering wheel, and the difference is estimated as the friction torque $T_{fric}$ produced by Coulomb friction inside of the steering system.

When the estimated value of SAT $T_{SAT}$ produced in steering the steering wheel in the left direction is defined as positive, the estimated value of SAT $T_{SAT}$ produced in steering the steering wheel in the right direction is defined as negative, and sine of the steering angular velocity signal supplied from the steering angular velocity sensor is reverted, a maximum value of the estimated value of SAT $T_{SAT}$ at and after the timing is calculated as follows.

When the steering angular velocity signal is reverted from negative to positive and the steering wheel is steered in the left direction (positive direction), the positive estimated value of SAT $T_{SAT}$ is produced, and therefore the maximum value $T_{max}$ of the estimated value of SAT $T_{SAT}$ is calculated by the following equation.

$$T_{max}(k) = \begin{cases} T_{max}(k-1) & \text{(when } T_{SAT}(k) \leq T_{max}(k-1)) \\ T_{SAT}(k) & \text{(when } T_{SAT}(k) > T_{max}(k-1)) \end{cases}$$

Next, when it is detected that the steering angular velocity is reverted from positive to negative by steering back the steering wheel, the friction torque $T_{fric}$ is calculated by the following equation by using the estimated value of SAT $T_{SAT}$ at that point and the maximum value $T_{max}$ calculated as described above.

$T_{fric}(k)=T_{max}(k)-T_{SAT}(k)$

Meanwhile, when the steering angular velocity is reverted from positive to negative and the steering wheel is steered in the right direction, the negative estimated value of SAT $T_{SAT}$ is produced, and therefore a minimum value $T_{min}$ of the estimated value of SAT $T_{SAT}$ is calculated by the following equation.

$$T_{min}(k) = \begin{cases} T_{min}(k-1) & \text{(when } T_{SAT}(k) \geq T_{min}(k-1)) \\ T_{SAT}(k) & \text{(when } T_{SAT}(k) < T_{min}(k-1)) \end{cases}$$

Next, when it is detected that the steering angular velocity is reverted from negative to positive by steering back the steering wheel, the friction torque $T_{fric}$ is calculated by the following equation by using the estimated value of SAT $T_{SAT}$ at that point and the minimum value $T_{min}$ calculated as described above.

$T_{fric}(k)=T_{SAT}(k)-T_{min}(k)$

As a result, with regard to the hysteresis characteristic produced each time the steering wheel is steered back, the friction torque $T_{fric}$ is estimated each time the steering wheel is steered back, and therefore the accurate magnitude of the hysteresis characteristic can always be estimated.

Particularly, when driving on a rough road, road disturbance is operated as dithering effect with regard to the Coulomb friction inside of the steering system, the term of the Coulomb friction is reduced, and the Coulomb friction is changed. Hence, if the friction torque $T_{fric}$ is estimated each time the steering wheel is steered back as described above, even when the magnitude of the Coulomb friction is changed, a newest compensation of the hysteresis characteristic can successively be carried out.

According to the first embodiment, an explanation has been given of an example of estimating the grip state by using the model of calculating the slip angle from SAT, removing the hysteresis characteristic by calculating the slip angle reference value constituting the output of the model when the input is constituted by SAT having the hysteresis characteristic, and comparing the slip angle reference value and the estimated value of the slip angle. A second embodiment explained below, estimates the grip state as the road surface friction condition by directly removing the hysteresis characteristic from SAT that has the hysteresis characteristic and using the corrected value of SAT, with the hysteresis characteristic removed therefrom, and the slip angle.

Figure 14:
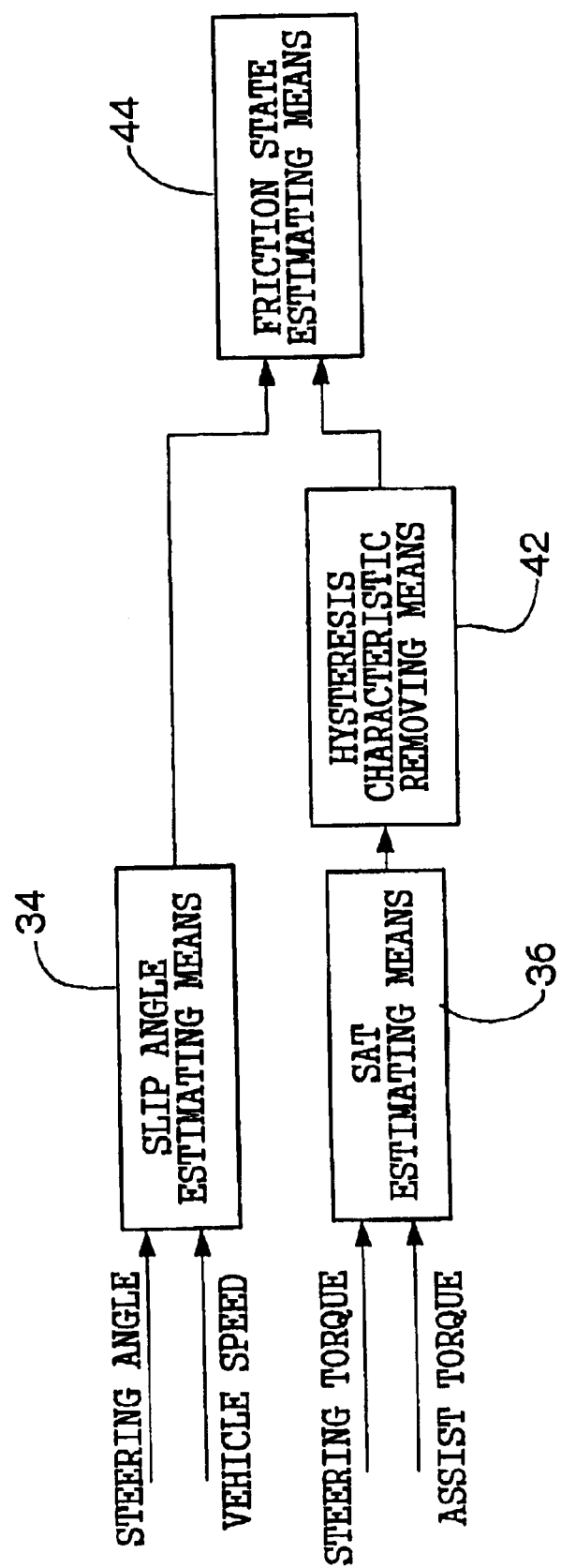
FIG. 14 is a block diagram showing a second embodiment of the invention applied to a vehicle mounted with an electric power steering apparatus.

An explanation of the embodiment will be given in reference to FIG. 14. According to the embodiment, in place of the slip angle reference calculating means shown in FIG. 1 when the microcomputer is considered by functional blocks, a hysteresis characteristic removing means 42 is provided for removing the hysteresis characteristic from SAT, and in friction state estimating means 44, the road surface friction condition, including the grip state, is estimated based on the corrected value of SAT, with the hysteresis characteristic removed therefrom, and the estimated value of the slip angle, estimated by the slip angle estimating means 34.

An explanation will now be given of operation of the respective means. The hysteresis characteristic removing means 42 removes influence of Coulomb friction of the power steering apparatus, which causes generation of the hysteresis characteristic, from an estimated value of SAT, which has the hysteresis characteristic, estimated by the SAT estimating means 36, and outputs the estimated value of SAT, with the hysteresis characteristic removed therefrom, as the corrected value of SAT.

The friction state estimating means 44 calculates and outputs the grip state as the road surface friction condition, as follows, from the slip angle and the corrected value of SAT with the hysteresis characteristic removed therefrom.

Calculation for removing the hysteresis characteristic by the hysteresis characteristic removing means 42, is carried out according to the following logic. The logic is a calculating equation having a gradient represented by a ratio of a change in the corrected value of SAT to a change in the estimated value of SAT, for calculating the gradient $K_1$ of a region in which the estimated value of SAT varies due to Coulomb friction by the calculating equation, which differs for respective regions, having a gradient smaller than a gradient of a region other than the region (=1).

Figure 15:
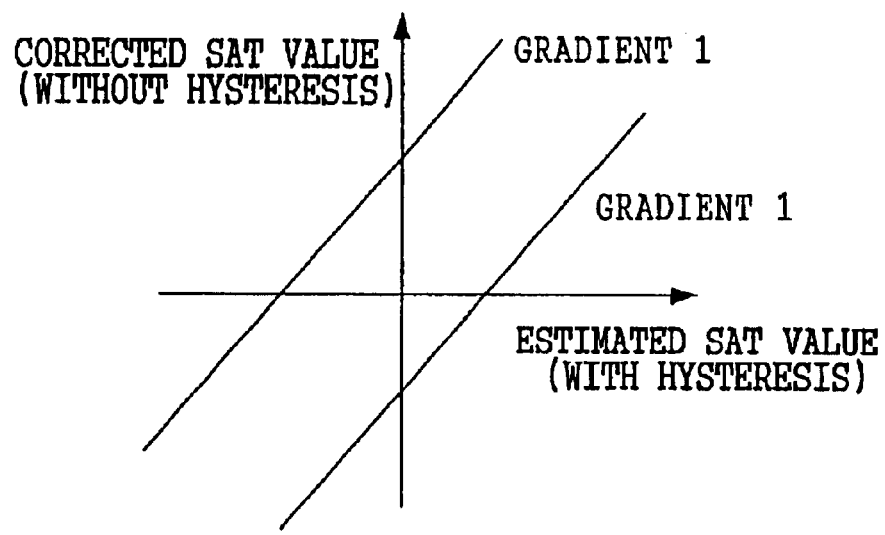
FIG. 15 is a graph showing an upper limit and a lower limit of a corrected value of SAT.

FIG. 15 shows a coordinate plane showing a relationship between the estimated value of SAT that has the hysteresis characteristic, and the estimated value of SAT with the hysteresis characteristic removed therefrom (corrected value of SAT), and a width between two straight lines on the coordinate plane represents the magnitude of the hysteresis characteristic. The estimated value of SAT that has the hysteresis characteristic and the estimated value of SAT with the hysteresis characteristic removed therefrom differ from each other in magnitude by the amount of the hysteresis characteristic, and therefore gradients of the respective straight lines are 1.

Figure 16:
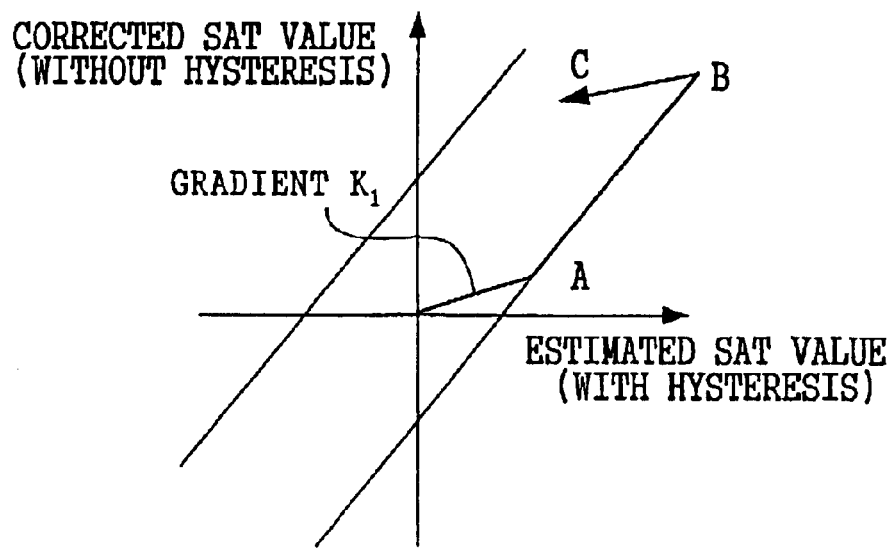
FIG. 16 is a diagram explaining a method for calculating the corrected value of SAT from an estimated value of SAT.

FIG. 16 shows a method of calculation for removing the hysteresis characteristic. In a straight driving state in which both of the estimated value of SAT and the slip angle become 0, the hysteresis characteristic is not generated, and 0 is outputted as the corrected value of SAT at this time. Next, when steering is carried out and SAT is generated, the corrected value of SAT is calculated by the gradient of $K_1$ relative to the estimated value of SAT. In the computer, calculation is carried out by the digitized logic in accordance with equation (16) shown below.

$$T_{SAT0}(k+1)=T_{SAT0}(k)+K_1 \cdot (T_{SAT}(k+1)-T_{SAT}(k)) \qquad (16)$$

In the equation, $T_{SAT0}$ is the corrected value of SAT with the hysteresis characteristic removed therefrom. The gradient $K_1$ is set to be smaller than 1, whereby a variation in the corrected value of SAT is reduced even when the estimated value of SAT varies due to Coulomb friction.

Equation (16), mentioned above, shows that it is determined whether the current value of the estimated value of self aligning torque falls in the hysteresis region due to Coulomb friction from a current value of the estimated value of self aligning torque, a preceding value of the estimated value of self aligning torque and a preceding value of the corrected value of self aligning torque. A current value of the corrected value of self aligning torque is calculated such that when the estimated value of self aligning torque falls in the hysteresis region, a magnitude of a change in the corrected value, calculated by a difference between the current value of the corrected value of self aligning torque and the preceding value of the corrected value of self aligning torque, becomes smaller than a magnitude of a change in the estimated value, calculated by a difference between the current value of the estimated value of self aligning torque and the previous value of the estimated value of self aligning torque, and when the estimated value of self aligning torque falls outside of the hysteresis region, the change in the corrected value and the change in the estimated value coincide with each other.

Further, when steering is carried out and the calculated value of the corrected value of SAT by equation (16) reaches point A in FIG. 16 and the estimated value of SAT is increased, the corrected value of SAT is increased in accordance with the following equation along the straight line indicating the lower limit of the model.

$$T_{SAT0}(k+1)=T_{SAT0}(k)+T_{SAT}(k+1)-T_{SAT}(k) \qquad (17)$$

Further, when steering is further carried out and an increase in steering is finished at a location of reaching point B and the estimated value of SAT starts reducing, the corrected value of SAT is reduced in accordance with equation (16) by the gradient $K_1$. At the region, a variation in the corrected value of SAT is set to be smaller than the variation in the estimated value of SAT. According thereto, even when the steering force of the driver is more or less changed in the state of maintained steering in turning, the corrected value of SAT is not influenced by Coulomb friction. Further, when the estimated value of SAT is increased again at point C reached by reducing SAT from point B, the corrected value of SAT is calculated to increase to point B in accordance with equation (16). Further, when the estimated value of SAT is further reduced from point C by steering back and reaches the upper limit of the model, the corrected value of SAT is calculated to reduce in accordance with equation (17) along the straight line indicating upper limit. By setting the two kinds of gradients, the corrected value of SAT relative to the estimated value of SAT is uniquely determined and the hysteresis characteristic shown in FIG. 16 is removed.

Figures 17A, 17B:
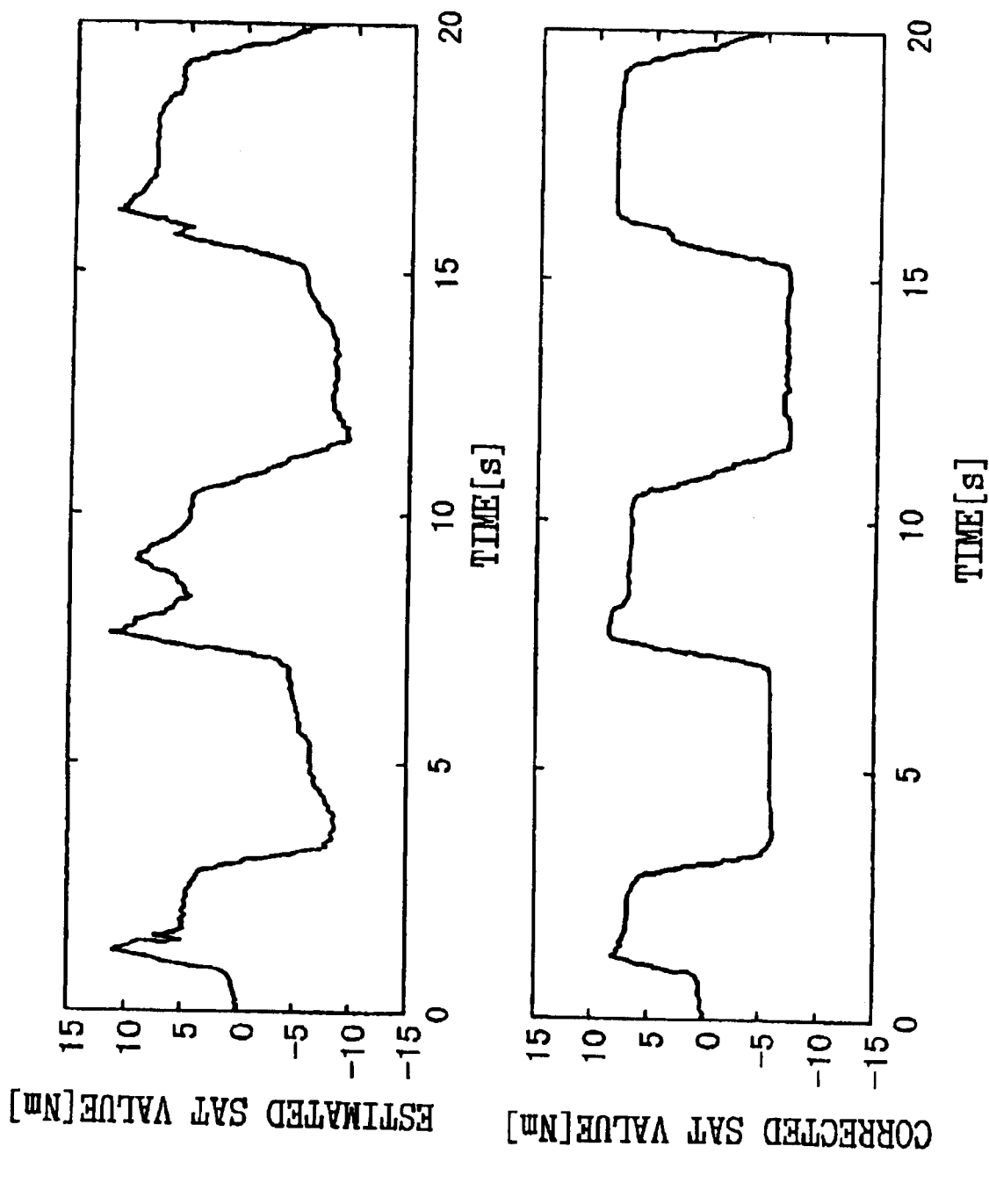
FIG. 17A is a graph showing change, over time, of the estimated value of SAT.
FIG. 17B is a graph showing change, over time, of the corrected value of SAT with a hysteresis characteristic removed therefrom.

FIG. 17A shows the estimated value of SAT in running on the high $\mu$ road and FIG. 17B shows the corrected value of SAT removed of the hysteresis characteristic based on equations (16) and (17) from the estimated value of SAT respectively. It is known that by comparing FIGS. 17A and 17B, by the effect of removing the hysteresis, the variation in maintaining steering which is regarded to be influenced by Coulomb friction, is substantially compensated for.

Figure 18B:
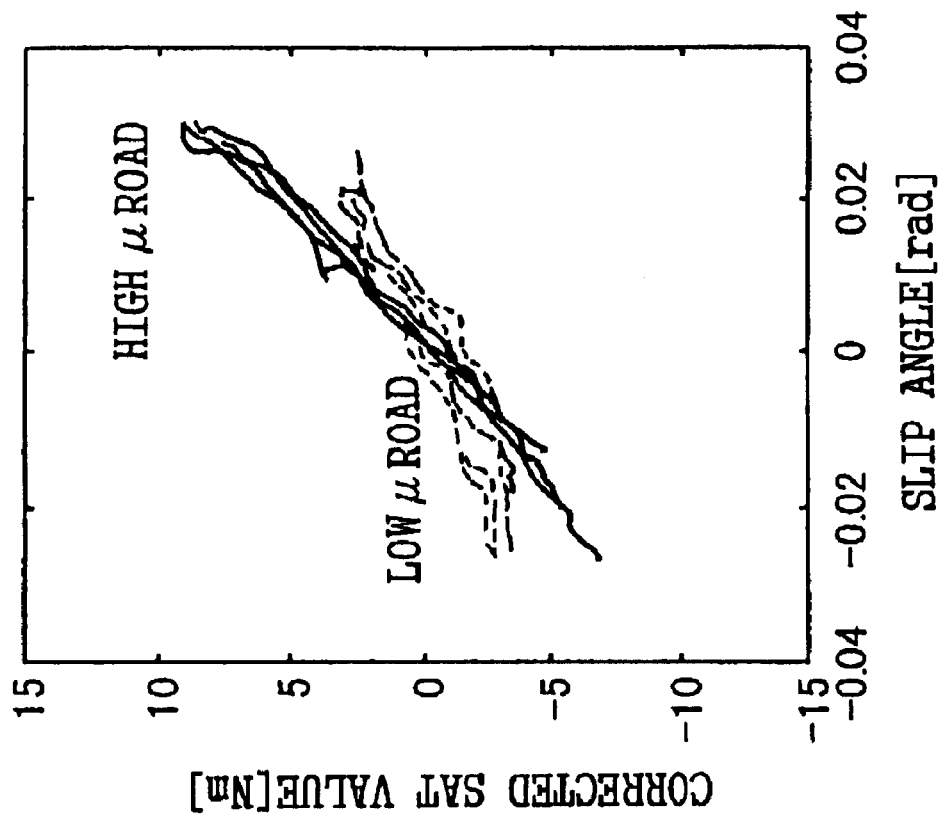
FIG. 18B is a graph showing a relationship between the slip angle and the corrected value of SAT on the high $\mu$ road and the low $\mu$ road.
Figure 18A:
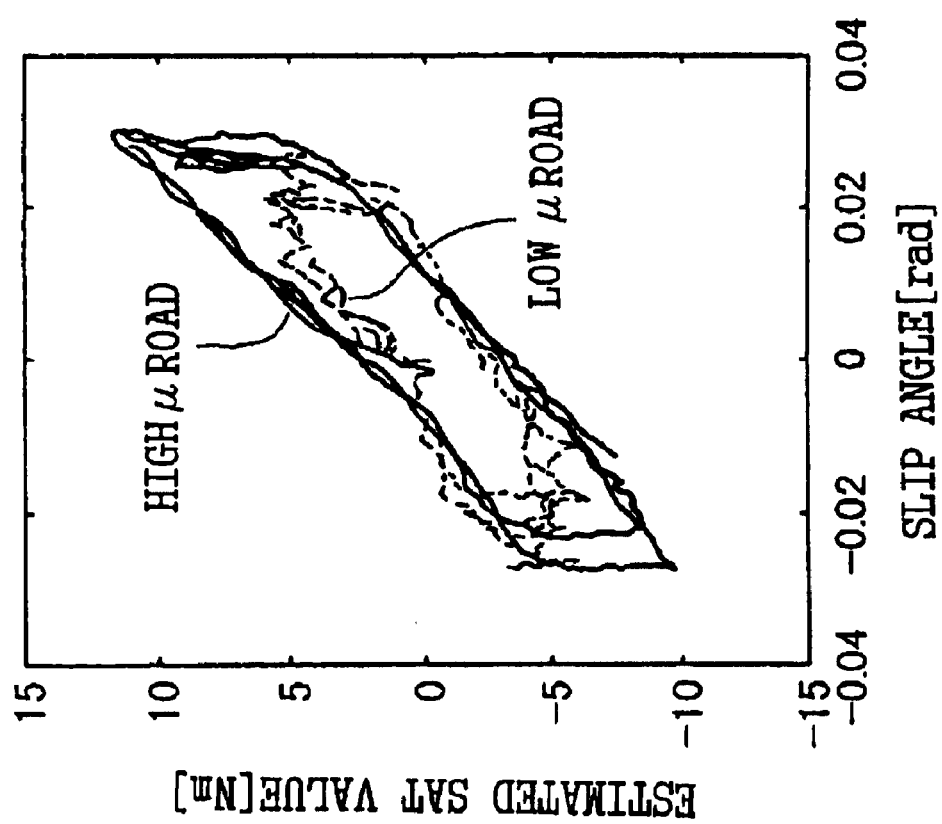
FIG. 18A is a graph showing a relationship between the slip angle and the estimated value of SAT on a high $\mu$ road and a low $\mu$ road.

Further, FIG. 18A shows a relationship between the slip angle and the estimated value of SAT in running on the high $\mu$ road and the low $\mu$ road and FIG. 18B shows a relationship between the slip angle and the corrected value of SAT, respectively. It can be understood from FIG. 18B that the relationship between the slip angle and the corrected value of SAT becomes substantially linear and the hysteresis characteristic is removed.

The road surface friction condition estimating means 44 calculates the grip state as the road surface friction condition as shown below based on the front wheel slip angle estimated by the slip angle estimating means 34 and the corrected value of SAT removed of the hysteresis characteristic.

That is, the road surface friction condition estimating means 44 compares the reference value of SAT derived by multiplying the slip angle by a coefficient which is changed in accordance with the vehicle speed or the kind of tire, and the corrected value of SAT and outputs the grip state in accordance with the difference between the reference value of SAT and the corrected value of SAT. The coefficient for deriving the reference value of SAT is set by assuming the high grip state and the corrected value of SAT becomes smaller than the reference value of SAT in the low grip state such as running on the low $\mu$ road. The road surface friction condition estimating means 44 calculates and outputs the road surface friction condition such that the larger the deviation between the absolute value of the reference value of SAT and the absolute value of the corrected value of SAT, the smaller the grip state, that is, the road surface friction condition becomes, by utilizing the property.

Figure 19A:
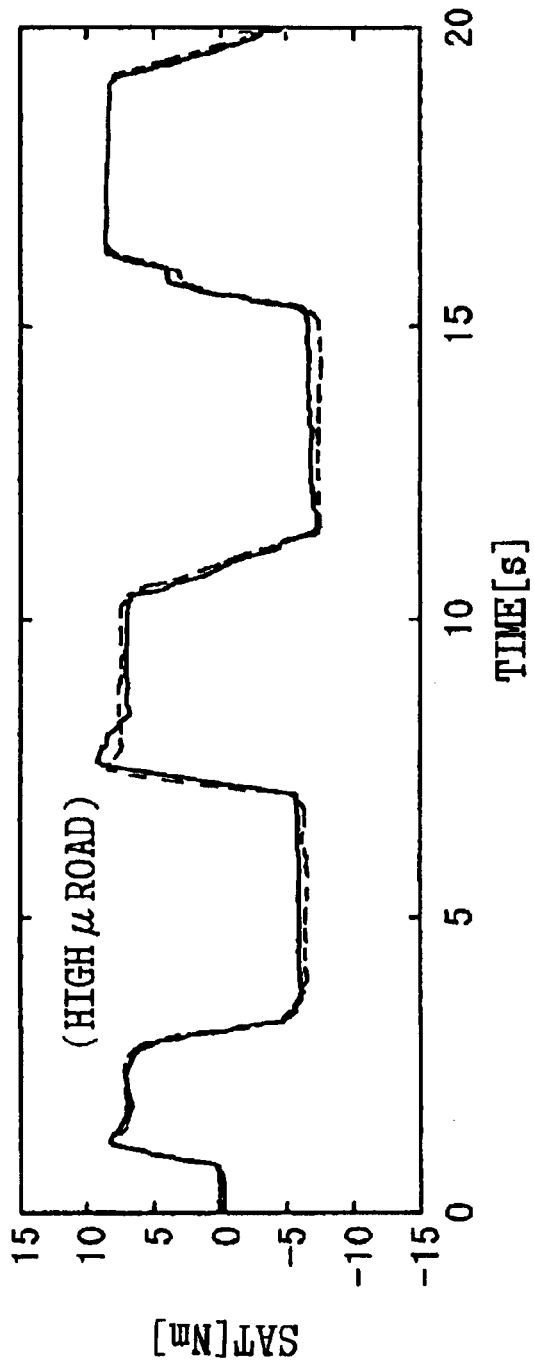
FIG. 19A is a graph showing change, over time, of a reference value of SAT and the corrected value of SAT when driving on a high $\mu$ road.
Figure 19B:
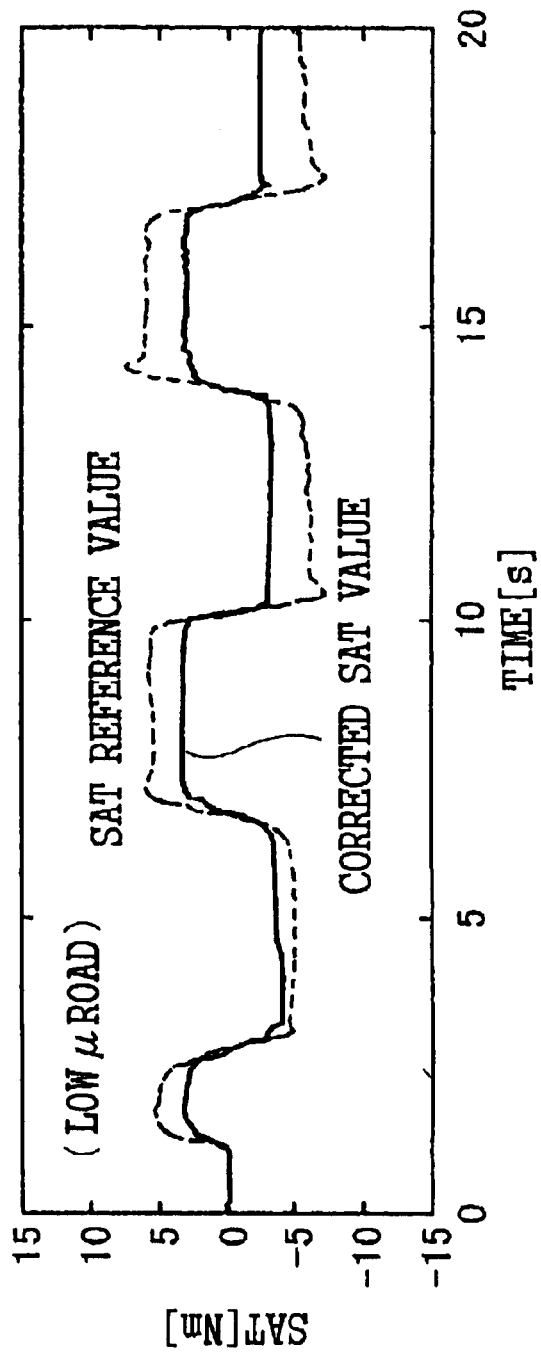
FIG. 19B is a graph showing change, over time, of the reference value of SAT and the corrected value of SAT when driving on a low $\mu$ road.

FIGS. 19A and 19B compare the corrected value of SAT (bold line) and the reference value of SAT (broken line) derived by multiplying the front wheel slip angle by the coefficient which is changed in accordance with the vehicle speed. It can be understood that whereas the reference value of SAT calculated from the slip angle assuming the high grip sate, substantially coincides with the corrected value of SAT in running on the high $\mu$ road as shown by FIG. 19A, in running on the low $\mu$ road in which the grip state is lowered, as shown by FIG. 19B, there is brought about a deviation between the reference value of SAT and the corrected value of SAT.

Figure 20:
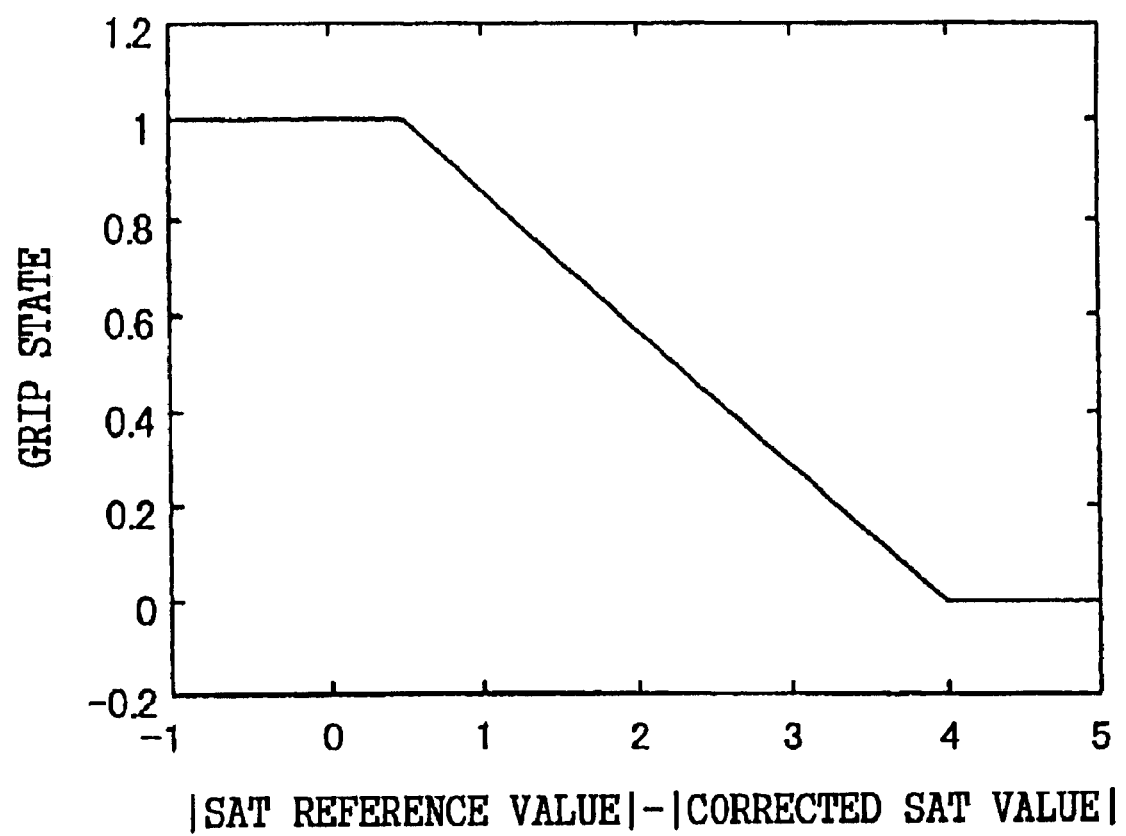
FIG. 20 is a graph showing a relationship between a difference between an absolute value of the reference value of SAT and an absolute value of the corrected value of SAT and a grip state.

Therefore, the road surface friction condition estimating means 44 calculates the road surface friction condition including the grip state from a graph shown in FIG. 20 by using a difference between respective absolute values of the corrected value of SAT and the reference value of SAT. The road surface friction condition including the grip state calculated here is normalized in a range of [0, 1], showing that the larger the value, the higher the grip state, that is, the road surface friction condition. According to the graph shown in FIG. 20, the larger the difference between the absolute value of the reference value of SAT and the absolute value of the corrected value of SAT, the smaller the grip state, that is, the road surface friction condition is estimated and the smaller the difference between the absolute value of the reference value of SAT and the absolute value of the corrected value of SAT, the larger the grip state, that is, the road surface friction condition is estimated.

Figure 21A:
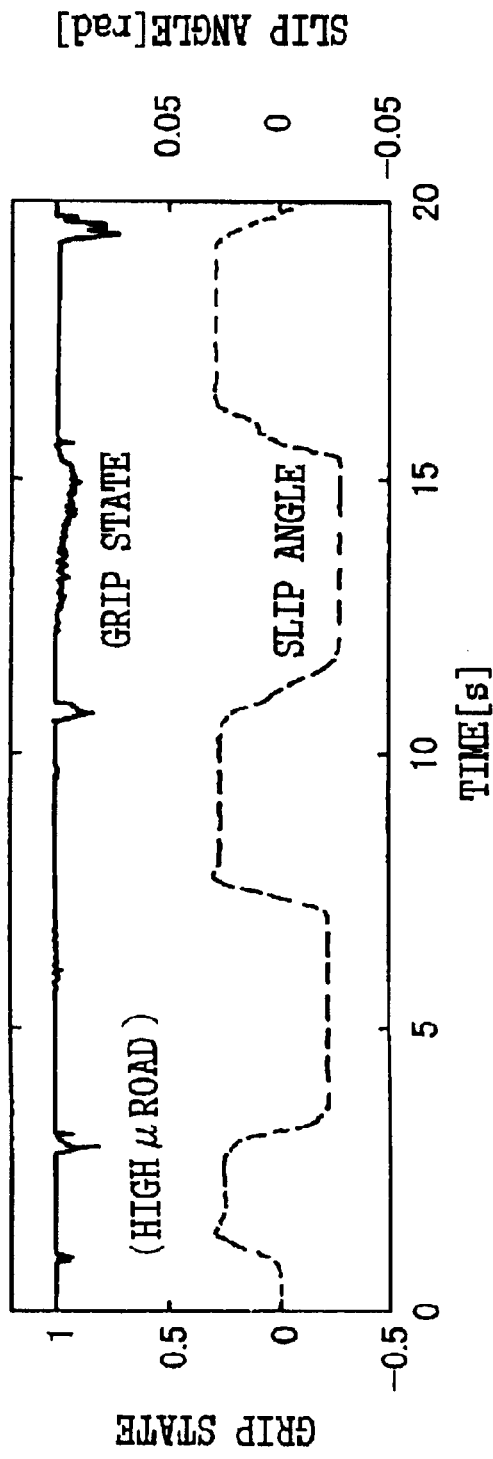
FIG. 21A is a graph showing the grip state and the estimated value of the slip angle when driving on a high $\mu$ road.
Figure 21B:
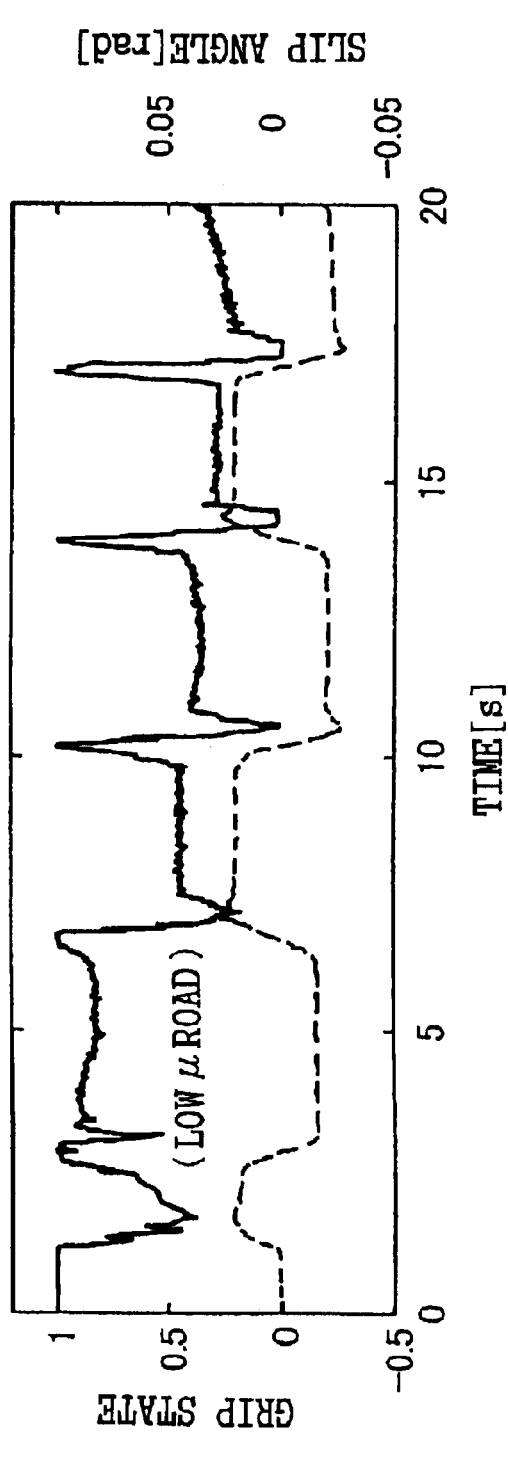
FIG. 21B is a graph showing the grip state and the estimated value of the slip angle when driving on a low $\mu$ road.

FIGS. 21A and 21B respectively show the grip state and the estimated value of the slip angle in running on the high $\mu$ road and the grip state and the estimated value of the slip angle in running on the low $\mu$ road. As shown by FIG. 21A, in running on the high $\mu$ road, in the case of the slip angle to this degree, it can be estimated that the always high grip state is brought about regardless of presence or absence of the slip angle. Further, as shown by FIG. 21B, in running on the low $\mu$ road, it can be understood that the grip state is lowered. Further, there can accurately be estimated the phenomenon by which the grip state become 1 at a time point at which the slip angle becomes near to 0 in steering and the grip state recovers in a region near to straight advancement.

Although an explanation has been given of respective examples of estimating the road surface friction condition including the grip state by comparing the slip angle with the model according to the first embodiment and comparing SAT with the model according to the second embodiment, the invention is not limited to the constitution of comparing with the model in this way, but the grip state may be described as a function of SAT and the slip angle after removing the hysteresis or the road surface friction condition including the grip state may be estimated by a two-dimensional graph of SAT and the slip angle after removing the hysteresis.

Further, although an explanation has been given of an example of applying the invention to the vehicle mounted with the electric power steering apparatus in the above-described, the invention is also applicable to a vehicle having a hydraulic power steering apparatus when hydraulic pressure of the power steering apparatus in correspondence with the steering torque and the assist torque can be measured.

Next, an explanation will be given of a third embodiment of applying the invention to a steering angle neutral point estimating apparatus. According to the embodiment, a position of a neutral point constituting a steering angle of a steering wheel by which the vehicle is brought into the straight advancement state is estimated by using the hysteresis characteristic removing means according to the second embodiment.

Figure 22:
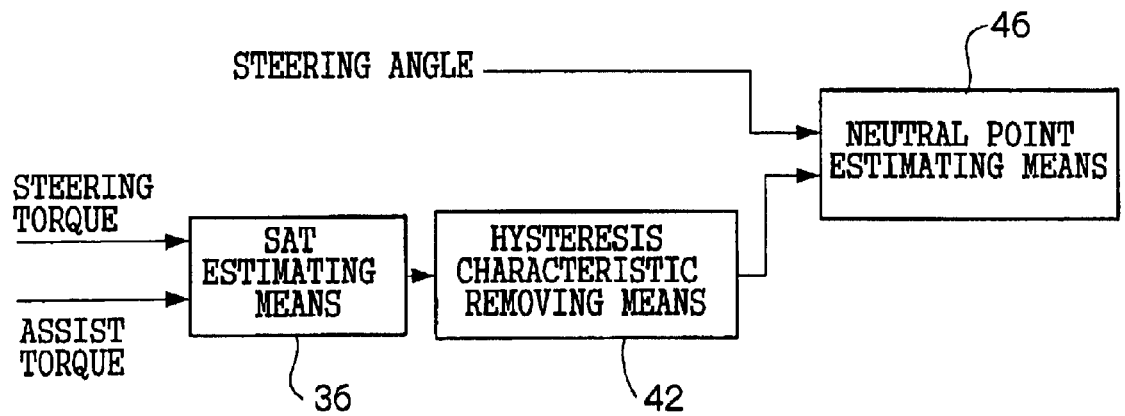
FIG. 22 is a block diagram showing a third embodiment of the invention applied to an apparatus for estimating a position of a neutral point of a steering wheel.

An explanation will be given of the embodiment in reference to FIG. 22 as follows. According to the embodiment, the slip angle calculating means 34 of FIG. 14 is omitted, neutral point estimating means 46 is provided in place of the friction state estimating means 44 and the position of the neutral point is estimated by the neutral point estimating means 46 by the steering angle and the corrected value of SAT which is the estimated value of SAT which is not provided with the hysteresis characteristic. Further, portions in FIG. 22 in correspondence with those in FIG. 14 are attached with the same notations and a detailed explanation thereof will be omitted.

An explanation will be given of operation of the respective means. As explained as mentioned above, the hysteresis characteristic removing means 42 removes influence of Coulomb friction of the power steering apparatus causing to bring about the hysteresis characteristic from the estimated value of SAT having the hysteresis characteristic estimated in the SAT estimating means 36 and outputs the estimated value of SAT which is not provided with the hysteresis characteristic as the corrected value of SAT. That is, as shown by FIG. 23, in the case in which the abscissa indicates the estimated value of SAT in the case of having the hysteresis characteristic and the ordinate indicates the estimated value of SAT in the case of not having the hysteresis characteristic, when the estimated value of SAT having the hysteresis characteristic becomes 0 from a negative value (when torque produced in steering to the right is made positive) and the steering angular velocity indicates a positive value equal to or larger than a constant value (when steering to the right is made positive), there is used a straight line of gradient 1 passing through point A shown in FIG. 23 and the corrected value of SAT removed of the hysteresis characteristic is calculated by an algorism similar to that explained in FIG. 16 of the second embodiment by constituting an initial value by point A.

Figure 23:
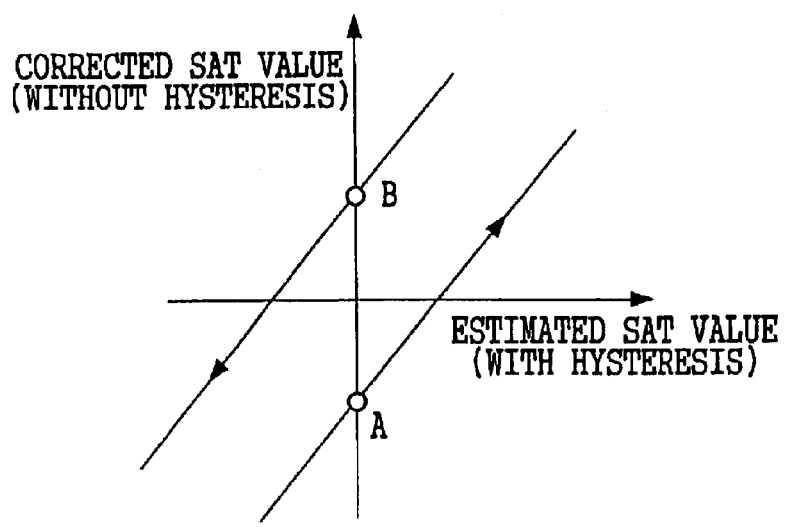
FIG. 23 is a graph explaining a method for calculating a corrected value of SAT from an estimated value of SAT.

Further, when the estimated value of SAT having the hysteresis characteristic becomes 0 from a positive value and the steering angular velocity indicates a negative value equal to or smaller than a constant value, the corrected value of SAT removed of the hysteresis characteristic is calculated by an algorism similar to that explained in FIG. 16 of the second embodiment by using a straight line of gradient 1 passing through point B shown in FIG. 23 and constituting an initial value by point B.

The neutral point estimating means 46 outputs a steering angle when the corrected value of SAT removed of the hysteresis characteristic becomes 0 as the neutral point.

The hysteresis characteristic is present (hysteresis characteristic is provided) between the steering angle and SAT or the steering torque and therefore, it is general to statistically estimate the neutral point from a frequency of the steering angle according to the related art. However, according to the conventional statistical method, there poses a problem that a long period of time is taken until finishing the estimation since the amount of data used is large and when running on a turning course, the error of estimation is produced by the deviation of the steering angle. In construct thereto, according to the embodiment, the neutral point is estimated from the relationship between the estimated value of SAT and the steering angle after removing the hysteresis characteristic and therefore, the neutral point can be estimated accurately and easily and the neutral point can be estimated in a short period of time without carrying out a statistical processing and without being influenced by the deviation of the steering angle.

Figure 24:
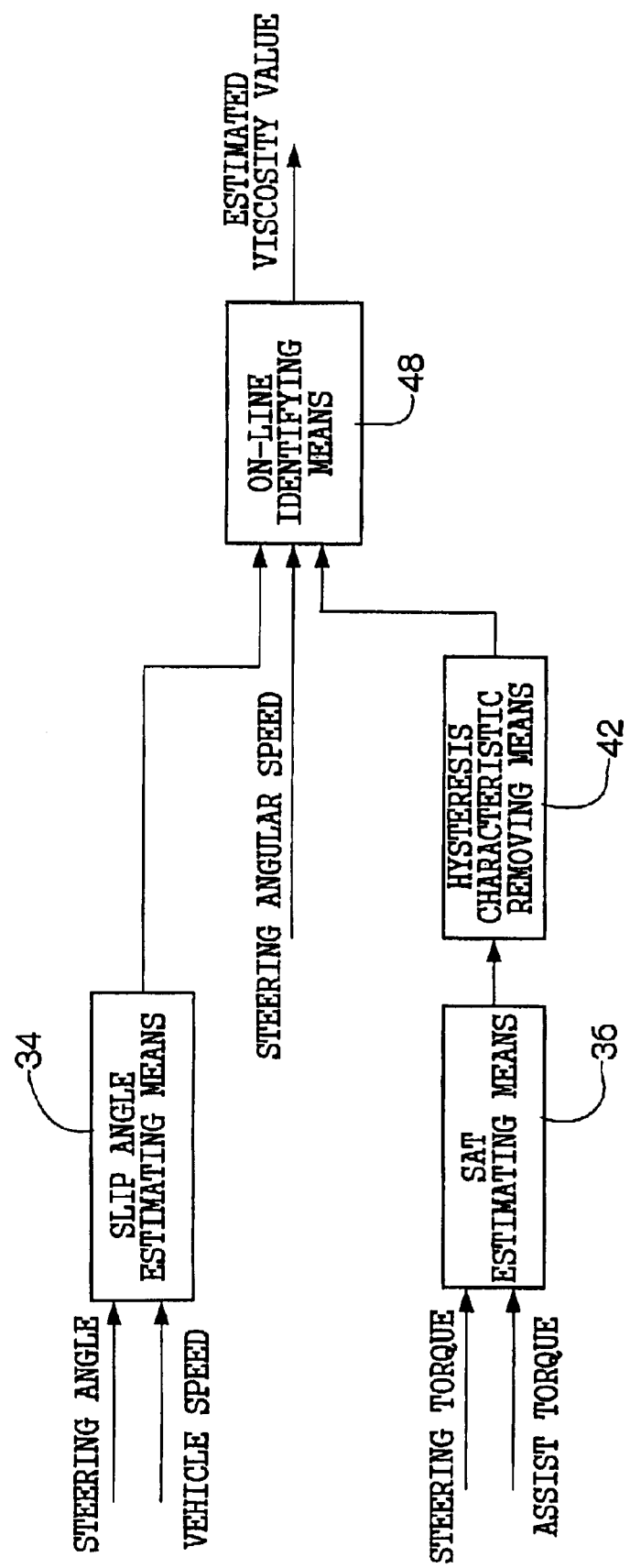
FIG. 24 is a block diagram showing a fourth embodiment of the invention applied to an apparatus for estimating viscosity in operating a steering wheel.

Next, an explanation will be given of a fourth embodiment of the invention. According to the embodiment, viscosity in steering the steering wheel is estimated by using the hysteresis characteristic removing means according to the second embodiment. According to the embodiment, as shown by FIG. 24, there is used on-line identifying means 48 in place of the friction state estimating means 44 of FIG. 14 and the viscosity in steering the steering wheel is estimated by inputting further a signal indicating the steering angular velocity to the on-line identifying means 48. Further, portions in FIG. 24 in correspondence with those of FIG. 14 are attached with the same notations and a detailed explanation thereof will be omitted.

The on-line identifying means 48 estimates the viscosity of the steering handle by applying an on-line identifying method based on the estimated value of SAT removed of the hysteresis characteristic by removing the hysteresis characteristic by the algorism explained above, the slip angle calculated by the slip angle calculating means 34 and the steering angular velocity.

According to the embodiment, the viscosity of the steering wheel is estimated by using the estimated value of SAT removed of the hysteresis characteristic (corrected value of SAT) and therefore, the hysteresis characteristic produced by Coulomb friction is removed and the accuracy of estimating the viscosity of the steering wheel can be promoted.

Figure 25:
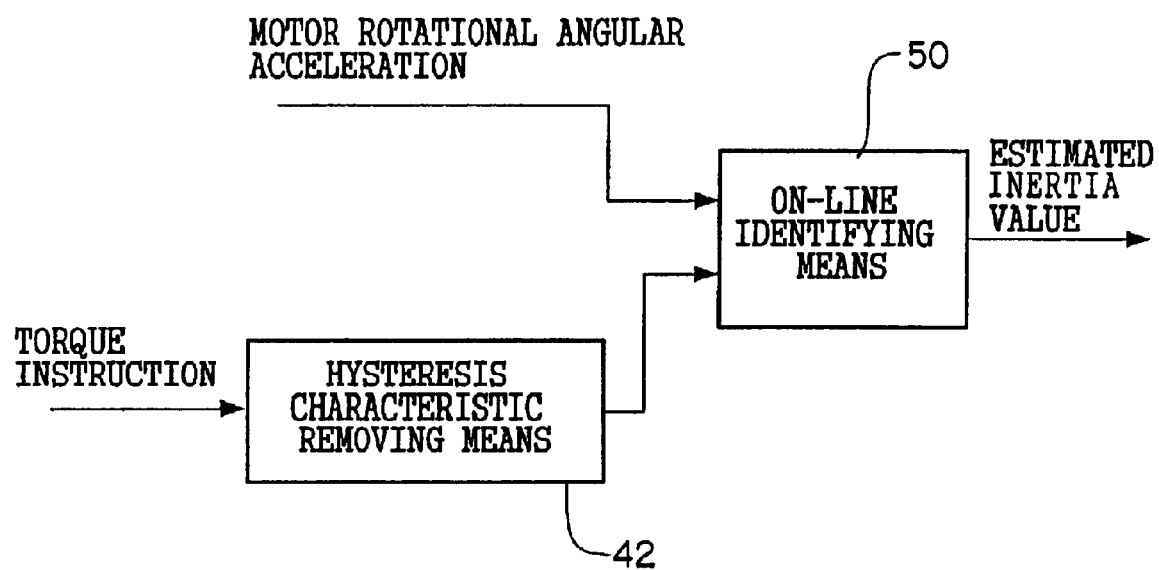
FIG. 25 is a block diagram showing another applied example of the invention.

The above-described hysteresis characteristic removing means is not limited to the case of removing the hysteresis characteristic produced by Coulomb friction of the steering wheel but is applicable to a number of systems including Coulomb friction. For example, the hysteresis characteristic removing means is applicable also to a case of estimating inertia of fingertip load of a robot in operation by on line. FIG. 25 shows a constitution when inertia of finger tip load is estimated by on line and the hysteresis removing means 42 estimates motor output torque T removed of an amount of Coulomb friction from torque instructed to a motor by the algorism explained above. Further, the on-line identifying means 50 estimates inertia J by applying the on-line identifying method based on equation J$\alpha$=T showing a relationship among the inertia J, the rotational angular velocity $\alpha$ of the motor and the output torque T from a time-sequential signal of the rotational angular velocity a of the motor and a time-sequential signal of the output torque T outputted from the hysteresis characteristic removing means 42.

Next, an explanation will be given of a fifth embodiment for determining a reduction in air pressure in reference to FIG. 26. According to the embodiment, as explained in reference to FIG. 14, there are provided SAT estimating means 36 for calculating the estimated value of SAT by adding the steering torque and the assist torque, SAT correcting means 41 for removing the hysteresis characteristic produced by friction of the steering system from the estimated value of SAT and estimating SAT produced between road and tire as the corrected value of SAT and the slip angle estimating means 34 for estimating the slip angle of the front wheel based on the steering angle and the vehicle speed. According to the embodiment, there is provided air pressure reduction determining means 54 for determining a reduction in air pressure based on the corrected value of SAT and the front wheel slip angle in place of the friction state estimating means of FIG. 14.

Next, an explanation will be given of the principle of estimating the air pressure reduction by the air pressure reduction determining means 54. According to the brush model theoretically describing a characteristic of force produced at tire, side force $F_{fy}$ and self aligning torque (SAT) $T_s$ are represented by the following equations.

$$F_{fy} = \begin{cases} \mu F_z(1-\xi^3) & (\xi > 0) \\ \mu F_z & (\xi \leq 0) \end{cases} \tag{18}$$

$$T_s = \begin{cases} \dfrac{bl^3 K_y}{12}\lambda\xi^3 & (\xi > 0) \\ 0 & (\xi \leq 0) \end{cases} \tag{19}$$

where, $$\xi = l - \dfrac{bl^2 K_y}{6\mu F_z}\lambda \tag{20}$$

where,
$F_z$: grounding load,
l: tire grounding length,
$K_y$: lateral rigidity of tread rubber per unit width and per unit length
b: width of grounding face
$\lambda$: lateral slip.

Although there is a relationship between the lateral slip $\lambda$ and the front wheel slip angle as follows, $$\lambda = \tan \alpha_f \tag{21},$$

generally, in a region of $\xi>0$, the slip angle $\alpha_f$ is small and therefore, $\lambda$ can be regarded as shown by equation (22) as follows.

$$\lambda \cong \alpha_f \tag{22}$$

From the above-described relationships, a gradient represented by a ratio $\partial F_{fy}/\partial \alpha_f$ of a very small change of the side force to a very small change of the slip angle at a vicinity of the slip angle of 0 (hereinafter, referred to as side force gradient), and a slop $\partial T_s/\partial \alpha_f$ represented by a ratio of a very small change of the corrected value of SAT to the very small change of the slip angle (hereinafter, referred to as gradient of corrected value of SAT), are respectively expressed as follows.

$$\dfrac{\partial F_{fy}}{\partial \alpha_f} = \dfrac{bl^2 K_y}{2} \tag{23}$$

$$\dfrac{\partial T_s}{\partial \alpha_f} = \dfrac{bl^3 K_y}{12} \tag{24}$$

Here, when the air pressure is reduced, the grounding length of the tire with respect to the road is increased and therefore, air pressure reduction of tire can be determined by calculating the side force gradient, the gradient of the corrected value of SAT and determining whether the side force gradient or the gradient of the corrected value of SAT is increased. According to the air pressure reduction determining apparatus of the embodiment, attention is paid to the characteristic and an increase in the grounding length accompanied by the pressure reduction is detected as an increase in the side force gradient or an increase in the gradient of the corrected value of SAT.

Further, from equation (23) and equation (24) described above, whereas the side force gradient is in proportion to square of the tire grounding length, the SAT gradient is in proportion to a cubic of the tire grounding length and the change in the tire grounding length is more significantly indicated by the SAT gradient and therefore, the reduction in the air pressure can be detected more accurately.

An explanation will be given of operation of the embodiment as follows. According to the embodiment, the reduction in the air pressure is determined based on the SAT gradient. The SAT estimating means 36 calculates the estimated value of SAT by adding the steering torque and the assist torque similar to that explained in reference to FIG. 14. The estimated value of SAT estimated here is a value including internal friction of the steering system and therefore, the SAT correcting means 41 removes the hysteresis characteristic caused by friction of the steering system from the estimated value of SAT and estimates SAT actually produced between road and tire as the corrected value of SAT. Further, the slip angle estimating means 34 estimates the slip angle of the front wheel based on the steering angle and the vehicle speed as explained in reference to FIG. 14.

The air pressure reduction determining means 54 detects an increase in the grounding length accompanied by the air pressure reduction explained in the above-described as an increase in a gradient of the corrected value of SAT based on the estimation principle as described above. That is, the air pressure reduction determining means 54 calculates the gradient of the corrected value of SAT with respect to the slip and from the front wheel slip angle and the corrected value of SAT and determines that the air pressure is reduced when the gradient of the corrected value of SAT becomes equal to or larger than a constant value.

The gradient of the corrected value of SAT can be estimated and calculated by using the on-line identifying method (on-line least squares method) explained above. The on-line least squares method estimates the gradient of the corrected value of SAT of FIG. 27B explained below and compares the estimated gradient and a constant value (a gradient of a one-dotted chain line representing a reference gradient).

When the on-line least squares method is used, the gradient can be estimated in a steering state by a small amount near to straight advancement and therefore, the air pressure reduction can be determined even in a running condition near to straight advancement. Further, since attention is paid only to the gradient of the corrected value of SAT, there is achieved an effect of capable of determining the air pressure reduction accurately without being influenced by a road cant even in a situation in which a segment of the SAT characteristic is shifted by the road cant as in running on a bank.

Further, although according to the embodiment, an explanation has been given of an example of determining the reduction in the air pressure by using the gradient of the corrected value of SAT, the embodiment is not limited thereto but the reduction in the air pressure of the tire may be determined when there is used the reference value of SAT set in accordance with the front wheel slip angle used in the above-described second embodiment, the reference value of SAT is compared with the corrected value of SAT and the corrected value of SAT becomes larger than the reference value of SAT. That is, the air pressure reduction determining means 54 may determine that the air pressure is reduced when a difference between the corrected value of SAT and the reference value of SAT is calculated and the difference exceeds a threshold or may determine that the air pressure is reduced when ratio of the corrected value of SAT to the reference value of SAT is calculated and the value exceeds a threshold. Further, the threshold used here may be set to be variable in accordance with the slip angle or the vehicle speed.

Figure 27A:
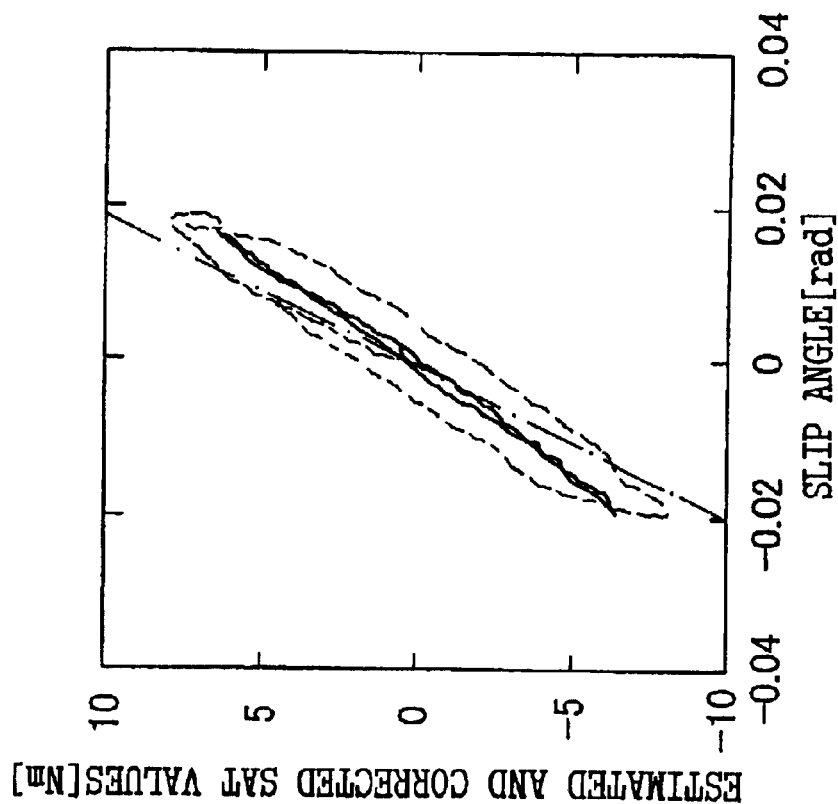
FIG. 27A is a graph showing a relationship between a steering angle and an estimated value of SAT.

FIG. 27A shows a relationship between the steering angle and the estimated value of SAT when stepped steering is repeated in running at constant vehicle speed (30 km/h) in a state in which the air pressure is normal, that is, a relationship between the steering angle and a value produced by adding the assist torque of the power steering to the steering torque of steering by the driver.

According to the related art described in JP-A Nos. 11-59466 and 11-334634, the reference torque indicated by a one-dotted chain line is set and it is determined that the air pressure is reduced when the estimated value of SAT exceeds the reference torque. However, as shown by FIG. 27A, there is present the hysteresis characteristic between the steering angle and the estimated value of SAT and therefore, although air pressure is normal, the reference value is exceeded in a transient state of steering.

Although according to the related art, prevention of erroneous operation in such a transient state is achieved by limiting the determination of the air pressure reduction in the case of maintaining steering, such a countermeasure limits a running condition which can be estimated and there poses a problem of a delay in determination.

Figure 27B:
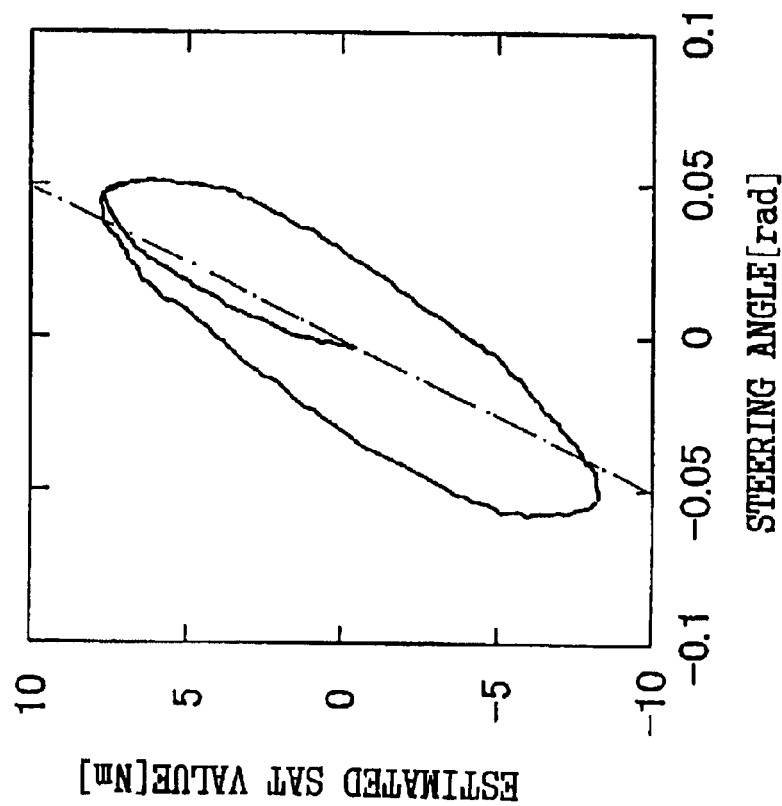
FIG. 27B is a graph showing a relationship between a slip angle and an estimated value of SAT and a corrected value of SAT.

In contrast thereto, according to the embodiment, when the estimated value of SAT and the reference value of SAT are used, as shown by FIG. 27B, the abscissa indicates the slip angle in place of the steering angle of FIG. 27A. The slip angle is a physical amount constituting a basis of producing lateral force of tire and there is not present a dynamic characteristic such as delay in time between the slip angle and SAT. In contrast thereto, there is present the dynamic characteristic between the steering angle and SAT accompanied by the movement of the vehicle between the steering angle and the slip angle and therefore, the influence of the dynamic property is effected.

According to the embodiment, the abscissa indicates the slip angle which is not influenced by the dynamic property of the motion of the vehicle and therefore, the air pressure reduction can be determined even in the transient state.

FIG. 27B shows a change in the estimated value of SAT (broken line) and the corrected value of SAT (bold line) removed of friction of the steering system when the abscissa indicates the slip angle as described above. It can be understood that by constituting the abscissa by the slip angle, bulging of the characteristic influenced by the dynamic characteristic of the motion of the vehicle is removed and a linear characteristic is provided.

Further, it can be understood that also the hysteresis characteristic is removed by removing friction of the steering system at the SAT correcting means 42. FIG. 27B simultaneously shows the reference value of SAT set at the air pressure reduction determining means 50 according to the embodiment by a one-dotted chain line. According to the experiment, the corrected value of SAT is always equal to or smaller than the reference value of SAT except a region at a vicinity of the original point and it can be understood that the determination of the air pressure reduction is accurately carried out in a wide region excluding the straight advancement state.

Figure 28:
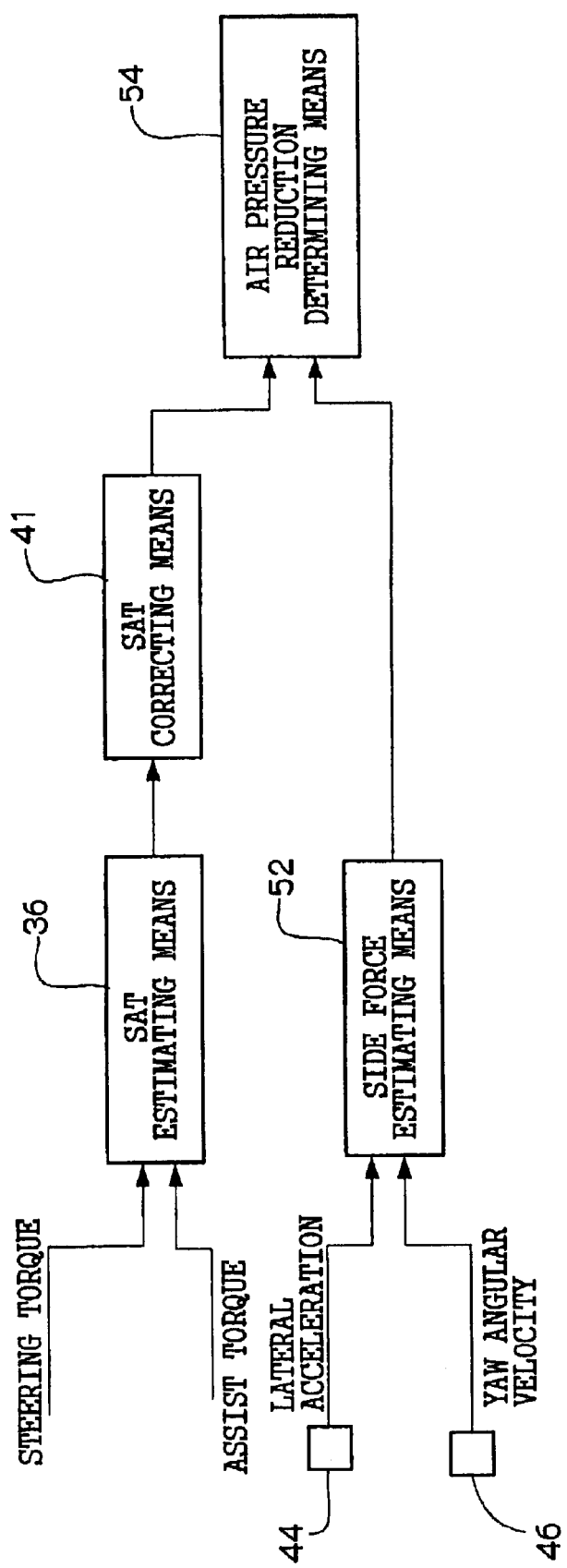
FIG. 28 is a block diagram showing a sixth embodiment of the invention applied to an apparatus for estimating a reduction in air pressure of a tire.

Next, an explanation will be given of a sixth embodiment of the invention in reference to FIG. 28. According to the embodiment, in place of the slip angle estimating means according to the fifth embodiment, there are provided a lateral acceleration sensor 44 for detecting lateral acceleration, a yaw angular velocity sensor 46 for detecting yaw angular velocity and side force estimating means 52 for estimating the side force of the front wheel based on the lateral acceleration of the yaw angular velocity.

The SAT estimating means 36 calculates the estimated value of SAT by adding the steering torque and the assist torque as described above. The estimated value of SAT estimated here is a value including internal friction of the steering system and therefore, the SAT correcting means 41 removes the hysteresis characteristic produced by friction of the steering system from the estimated value of SAT and estimates actual SAT produced between road and tire as the corrected value of SAT.

The side force estimating means 52 estimates the side force of the front wheel based on the lateral acceleration detected by the lateral acceleration sensor 44 and the yaw angular velocity detected by the yaw angular velocity sensor 46. The air pressure reduction determining means 54 determines reduction of the air pressure based on the corrected value of SAT and the side force of the front wheel.

Here, the side force (lateral force) $F_f$ of the front wheel can be calculated from equations of motion of the vehicle body shown by the following equations.

$$M\left(\frac{dv}{dt} + ru\right) = F_f + F_r \qquad (25)$$

$$I_z \frac{dr}{dt} = L_f F_f - L_r F_r \qquad (26)$$

However, the side force $F_f$ of the front wheel can be represented as shown by equation (27) shown below by simultaneously solving equations (25) and (26) and eliminating side force $F_r$ of the rear wheel.

$$F_f = \frac{L_r M g_y + I_z \frac{dr}{dt}}{L_f + L_r} \qquad (27)$$

where, $$g_y = \frac{dv}{dt} + ru$$

Further, M, v, r, u, $I_z$, $L_f$ and $L_r$ indicate physical amounts the same as those explained in equations (1) and (2), $F_f$ indicates side force of front wheel and $F_r$ indicates side force of rear wheel.

Figure 29:
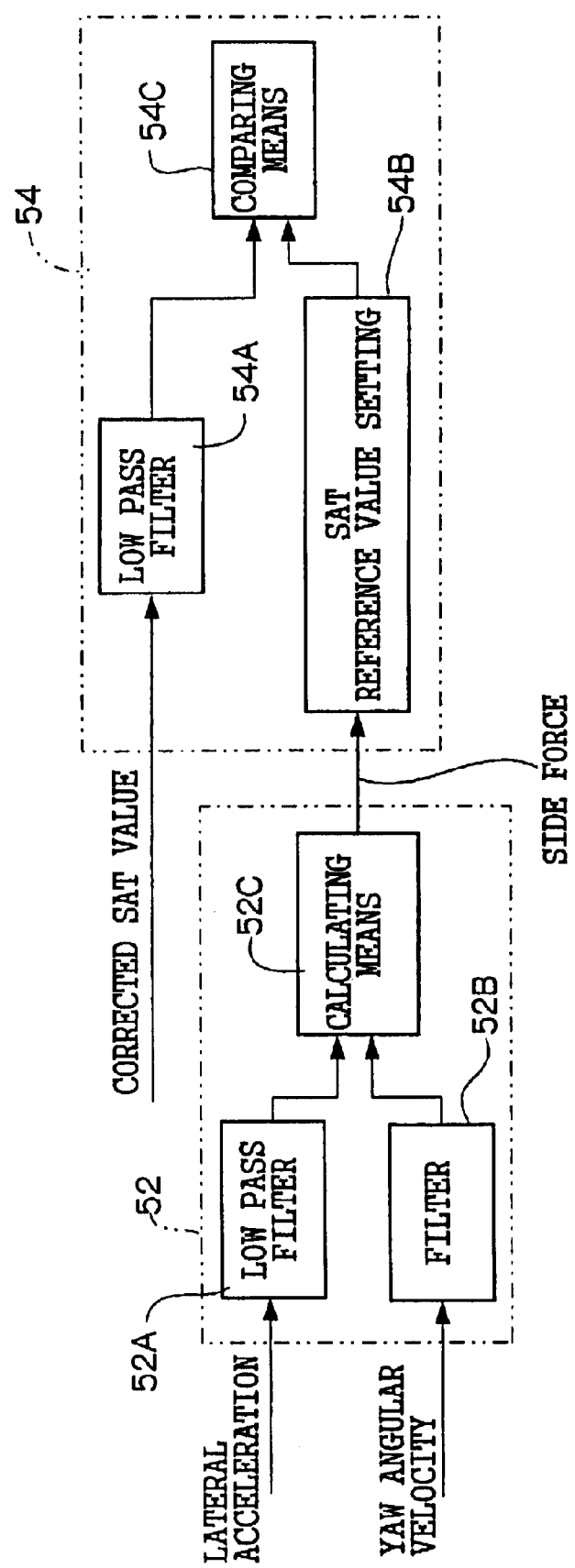
FIG. 29 is a block diagram showing details of side force estimating means and the air pressure reduction determining means of FIG. 28.

Therefore, as shown by FIG. 29, the side force estimating means 52 is constituted by a filter 52B for outputting a value approximated to a differential value dr/dt of the yaw angular velocity approximated by subjecting the yaw angular velocity to high pass or band pass filter processing based on equation (27), a low pass filter 52A for outputting a lateral acceleration subjected to low pass filter processing at a cutoff frequency the same as that of the filter processing to which the yaw angular velocity is subjected, and calculating means 52C for estimating the side force $F_f$ of the front wheel based on equation (27) from an output of the low pass filter 52A and an output of the filter 52B.

Further, the air pressure reduction determining means 54 is constituted by SAT reference value setting means 54B for setting the reference value of SAT in accordance with the side force of the front wheel, a low pass filter 54A for subjecting the corrected value of SAT to low pass filter processing by a cutoff frequency the same as that of the filter processing to which the low angular velocity is subjected, and comparing means 54C for comparing the reference value of SAT set in accordance with the side force of the front wheel and the corrected value of SAT produced by being subjected to low pass filter processing by the low pass filter 54A and determining that the air pressure is reduced when the corrected value of SAT becomes larger than the reference value of SAT.

According to the comparing means 54C, it is possible that a difference between the corrected value of SAT and the reference value of SAT is calculated and it is determined that the air pressure is reduced when the difference exceeds a threshold, or a ratio of the corrected value of SAT to the reference value of SAT is calculated and it is determined that the air pressure is reduced when a value of the ratio exceeds a threshold. Further, the threshold used here may be set variably in accordance with the slip angle or the vehicle speed.

Figure 30:
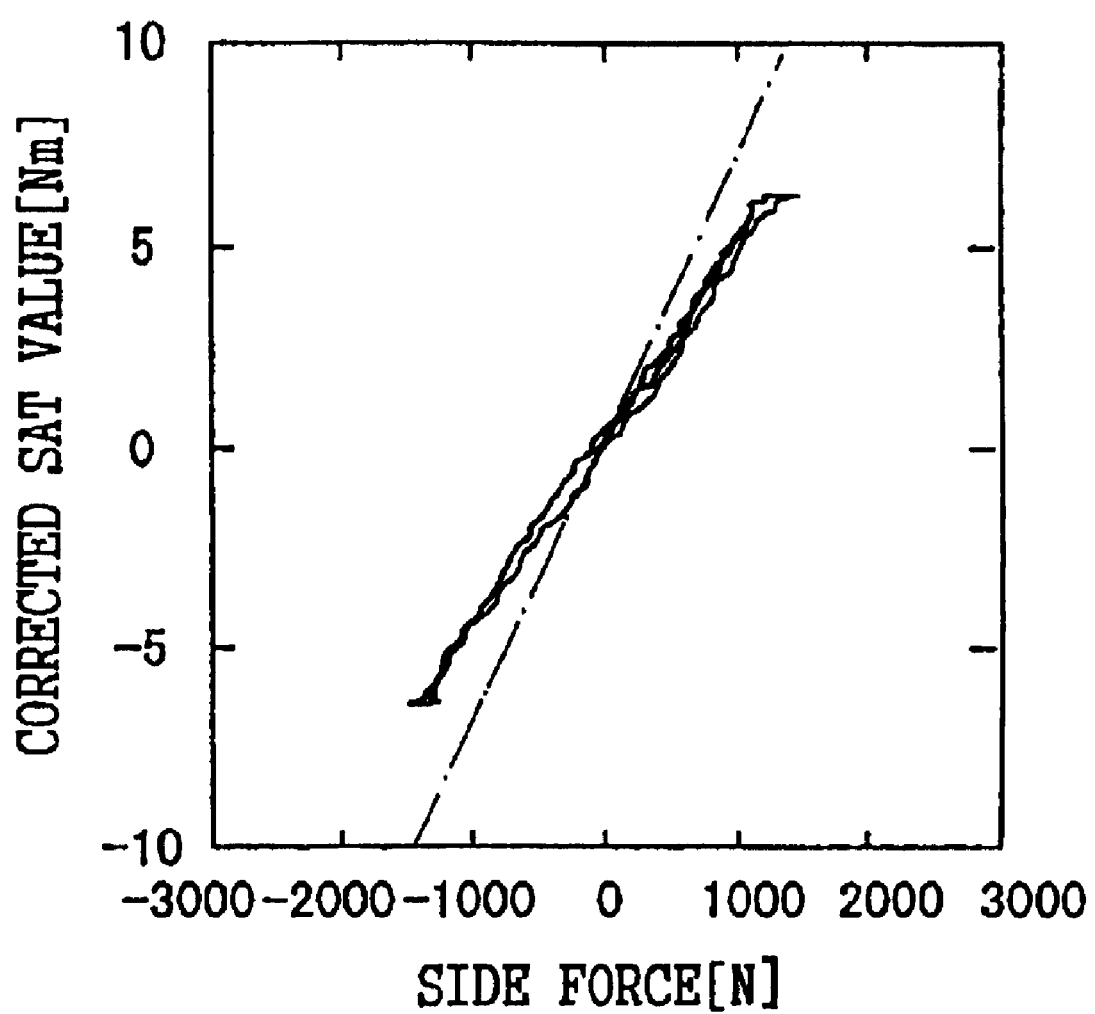
FIG. 30 is a graph showing a relationship between side force and a corrected value of SAT.

FIG. 30 shows the corrected value of SAT when the abscissa indicates the side force of the front wheel estimated in accordance with equation (27). It can be understood that also in the case of constituting the abscissa by the side force, similar to the case of constituting the abscissa by the slip angle, the hysteresis characteristic of SAT is removed by removing friction of the steering system. FIG. 30 simultaneously shows the reference value of SAT set by the SAT reference value setting means 54B of the air pressure reduction determining means 54 according to the embodiment by a one-dotted chain line.

According to the experiment, the corrected value of SAT is always equal to or smaller than the reference value of SAT except a region at a vicinity of the original point and it can be predicted that the air pressure reduction is determined in a wide region except the straight advancement state.

Meanwhile, although the constitution of the above-described fifth embodiment is characterized in that it is not necessary to provide sensors for measuring amounts of the state of motion of the vehicle such as the yaw angular velocity and the lateral acceleration, there also poses a problem that there is effected influence of error in estimating the slip angle accompanied by the air pressure reduction. That is, cornering stiffness constituting a parameter of equations of motion of the vehicle, is the same as the gradient of the side force and the gradient of the side force is influenced by the change of the grounding length of tire accompanied by the change of the air pressure as shown by equation (23). Therefore, the dynamic characteristic of the motion of the vehicle is also influenced by the change of the air pressure, for example, the magnitude of the slip angle in the case of steering under the same condition differs by a state in which air pressure of four wheels is simultaneously reduced such as natural air leakage and by a state in which the air pressure is lowered only at a single wheel of the front wheel by puncture or the like.

With regard thereto, according to the fifth embodiment, the slip angle is estimated based on the vehicle movement model fixed with parameters and therefore, the same value is outputted both in the state in which the air pressure is reduced simultaneously at four wheels and a state in which the air pressure is reduced only at a single wheel of the front wheel. It seems that a result of the calculation can constitute a factor of error in determining the air pressure reduction.

With regard thereto, according to the sixth embodiment, there is used the side force estimated and calculated based on equation (27). As is apparent from equation (27), the side force is not influenced by the cornering stiffness as a result of deriving the side force directly from the dynamic characteristic of the motion of the vehicle reflecting the actual side force. Therefore, the side force can be estimated always accurately regardless of different situations of the state in which the air pressure of the four wheels are simultaneously reduced and the state in which the air pressure is reduced only at the single wheel of the front wheel.

Further, according to the air pressure reduction determining means 54, it is also possible that the SAT reference value setting means 54B is not used, from the side force of the front wheel and the corrected value of SAT subjected to the low pass filter processing having a cutoff frequency the same as that of the filter subjected to the yaw angular velocity, there is calculated the gradient of the corrected value of SAT with regard to the side force represented by a ratio of the very small change of the corrected value of SAT to the very small change of the side force and when the gradient of the corrected value of SAT with regard to the side force becomes equal to or larger than a constant value, it is determined that the air pressure is reduced.

Further, the gradient of the corrected value of SAT with regard to the side force can be estimated by a calculation in which the slip angle of the algorism of calculating the gradient of the corrected value of SAT with regard to the slip angle, is substituted for the side force. Further, in the case of properties of SAT and the side force, the characteristics are not influenced by the road cant in running on a bank and therefore, an intercept of the estimation parameter may be fixed to 0. In this case, the estimated parameter of the on-line least squares method is constituted only by the gradient and an effect of reducing the calculation load can also be expected. A detailed explanation will be given of the algorism as follows.

Here, assume that the following relationship is established in SAT and side force.

$$T_s = k \cdot F_{fy} \quad (28)$$

Incidentally, k indicates the gradient of the corrected value of SAT with regard to the side force. When the on-line least square method is applied to equation (28) at this occasion, equation (29) is provided as follows.

$$L[i] = \frac{P[i-1] \cdot F_{fy}[i]}{\lambda_f + F_{fy}[i]^2 \cdot P[i-1]} \quad (29)$$

$$P[i] = \frac{1}{\lambda_f}(1 - L[i] \cdot F_{fy}[i]) \cdot P[i-1] \quad (30)$$

$$k[i] = k[i-1] + L[i] \cdot (T_s[i] - F_{fy}[i] \cdot k[i-1]) \quad (31)$$

where, $\lambda_f$ indicates forgetting factor.

According to the method, the gradient of the corrected value of SAT of FIG. 30 is estimated and the estimated gradient is compared with a predetermined value (gradient shown by one-dotted chain line). When the method is used, the gradient can be estimated even in a state of steering by a small amount near to straight advancement and therefore, the air pressure reduction can be determined even in a running condition near to straight advancement. Further, when described by the brush model, the gradient k of the corrected value of SAT with regard to the side force is shown below from equations (27) and (28).

$$k = \frac{l}{6} \quad (32)$$

This signifies that only the grounding length can be detected without depending on the rigidity of the tread rubber and the grounding width. Therefore, in the case of the method of deriving the gradient of the corrected value of SAT with regard to the side force, the reduction of the air pressure can accurately be determined without depending on the kind of tire and the size of tire such as studless tire or summer tire.

As has been explained above, according to the embodiment, the estimation can be carried out without being influenced by the variation in the steering torque of the driver when steering is maintained and further, the estimation can be carried out even in steering comparatively fast as in changing a lane.

Therefore, since friction of the steering system is removed by the SAT correcting means, even when the steering torque is varied by the driver to a degree by which the steering wheel is not moved when steering is maintained, the amount of variation is removed as friction and therefore, the corrected value of SAT is maintained constant and the pressure reduction can accurately be determined.

Further, there is estimated the slip angle of the front wheel constituting the basis of the force produced at the tire and air pressure reduction is determined from the relationship between the slip angle and the corrected value of SAT and therefore, the estimated value is not influenced by the dynamic characteristic of the movement of the vehicle and the determination can be carried out accurately even in the fast steering state.

Further, according to the embodiment, the gradient of the side force with regard to slip angle may be calculated according to the equation (23) and the air pressure may be determined to be reduced when the gradient of the side force becomes equal to or larger than a predetermined value.

As explained above, when the air pressure of the tire is reduced, the grounding length between tire and road is prolonged and therefore, it can be regarded equivalently that friction coefficient between tire and road is increased and air pressure reduction of tire and the road surface friction condition are brought into a close relationship. Therefore, the embodiment explained with regard to estimation of the road surface friction condition can be used in estimating the air pressure of tire and the embodiment explained with regard to estimation of air pressure reduction of tire can be used in estimating the road surface friction condition.

What is claimed is:

1. A physical amount estimating apparatus comprising:
    first outputting means for outputting a first physical amount that does not include a hysteresis characteristic;
    second outputting means for outputting a second physical amount that has a predetermined physical relationship to the first physical amount and includes a hysteresis characteristic;
    hysteresis removing means for calculating a corrected value with the hysteresis characteristic removed therefrom, based on the second physical amount; and
    estimating means for estimating a third physical amount based on a physical relationship between the first physical amount and the corrected value, wherein:
    the first physical amount is a physical amount related to a steering state of a steered wheel;
    the second physical amount is an estimated value of a self aligning torque estimated from a steering torque and an assist torque;
    the corrected value is a corrected value of the self aligning torque calculated from the estimated value of the self aligning torque; and
    the third physical amount is a physical amount related to one of a wheel state and a road state while a vehicle is driven.

2. The physical amount estimating apparatus according to claim 1, further comprising:
    a lateral acceleration sensor for detecting a lateral acceleration;
    a yaw angular velocity sensor for detecting a yaw angular velocity;
    a torque sensor for detecting a steering torque;
    an assist torque sensor for detecting an assist torque of steering;
    side force estimating means for estimating a side force of a steered wheel based on the lateral acceleration and the yaw angular velocity;
    self aligning torque estimating means for estimating a self aligning torque based on the steering torque and the assist torque;
    hysteresis removing means for calculating a corrected value of the self aligning torque with a hysteresis characteristic removed therefrom, based on an estimated value of the self aligning torque; and
    air pressure reduction estimating means for estimating whether an air pressure of a tire is reduced, based on the corrected value of the self aligning torque and the side force.

3. The physical amount estimating apparatus according to claim 1, wherein the physical amount related to the steering state of the steered wheel is a slip angle.

4. The physical amount estimating apparatus according to claim 1, wherein the hysteresis removing means calculates the corrected value of the self aligning torque by calculating equations, which each include a gradient represented by a ratio of a change in the corrected value of the self aligning torque to a change in the estimated value of the self aligning torque, and which equations are different for respective regions due to a gradient in a region, where the estimated value of the self aligning torque varies due to Coulomb friction, being made smaller than gradients of regions other than the region.

5. The physical amount estimating apparatus according to claim 1 wherein:
the hysteresis removing means determines whether a current value of the estimated value of the self aligning torque falls in a hysteresis region due to the Coulomb friction, using the current value of the estimated value of the self aligning torque, a preceding value of the estimated value of the self aligning torque and a preceding value of the corrected value of the self aligning torque; and
the hysteresis removing means calculates the current value of the corrected value of the self aligning torque such that:
when the current value of the estimated value of the self aligning torque falls in the hysteresis region, a magnitude of change in the corrected value, calculated using a difference between the current value of the corrected value of the self aligning torque and the preceding value of the corrected value of the self aligning torque, becomes smaller than a magnitude of change in the estimated value, calculated using a difference between the current value of the estimated value of the self aligning torque and the previous value of the estimated value of the self aligning torque; and
when the current value of the estimated value of the self aligning torque falls outside of the hysteresis region, the change in the estimated value coincide with each other.

6. The physical amount estimating apparatus according to claim 1, wherein the estimating means estimates the physical amount related to one of a wheel state and a road state while the vehicle is driven, based on the physical amount related to the steering state of the steered wheel and the corrected value of the self aligning torque, or based on a reference value of the self aligning torque, which is set in accordance with the physical amount related to the steering state of the steered wheel, and the corrected value of the self aligning torque.

7. The physical amount estimating apparatus according to claim 1, wherein the estimating means estimates the physical amount related to one of a wheel state and a road state while the vehicle is driven, based on a gradient of the corrected value of the self aligning torque, represented by a ratio of a change in the corrected value of the self aligning torque to a change in the physical amount related to the steering state of the steered wheel.

8. The physical amount estimating apparatus according to claim 1 wherein
the corrected value is a reference value of a slip angle, calculated from the estimated value of the self aligning torque.

9. The physical amount estimating apparatus according to claim 8, wherein the hysteresis removing means calculates the reference value of the slip angle by calculating equations, which each include a gradient represented by a ratio of a change in the reference value of the slip angle to a change in the estimated value of the self aligning torque, and which equations are different for respective regions due to a gradient of a region, where the estimated value of the self aligning torque varies due to Coulomb friction, being made smaller than gradients of regions other than the region.

10. The physical amount estimating apparatus according to claim 8, wherein the physical amount related to the steering state of the steered wheel is a slip angle, and the estimating means estimates the physical amount related to one of the wheel state and the road state while the vehicle is driven, based on the slip angle of the steered wheel and the reference value of the slip angle.

11. The physical amount estimating apparatus according to claim 1, wherein the wheel state is a reduction in an air pressure of a wheel and the road state is a road surface friction condition.

12. The physical amount estimating apparatus according to claim 8, wherein the wheel state is a reduction in an air pressure of a wheel and the road state is a road surface friction condition.

13. The physical amount estimating apparatus according to claim 1, further comprising:
a steering angle sensor for detecting a steering angle;
a vehicle speed sensor for detecting a vehicle speed;
a torque sensor for detecting a steering torque;
an assist torque sensor for detecting an assist torque of steering;
slip angle estimating means for estimating a slip angle of a steered wheel, based on the steering angle and the vehicle speed;
self aligning torque estimating means for estimating a self aligning torque based on the steering torque and the assist torque;
hysteresis removing means for calculating a corrected value with a hysteresis characteristic removed therefrom, based on an estimated value of the self aligning torque; and
friction state estimating means for estimating a road surface friction condition from the corrected value and the slip angle.

14. The physical amount estimating apparatus according to claim 13, wherein the hysteresis removing means calculates a reference value of the slip angle with regard to the estimated value of the self aligning torque, based on a relationship between the estimated value of the self aligning torque and the slip angle, as the corrected value.

15. The physical amount estimating apparatus according to claim 14, wherein the reference value of the slip angle is calculated by calculating equations, which each include a gradient represented by a ratio of a change in the reference value of the slip angle to a change in the estimated value of the self aligning torque, and which equations are different for respective regions due to a gradient of a region, where the estimated value of the self aligning torque varies due to Coulomb friction, being made smaller than gradients of regions other than the region.

16. The physical amount estimating apparatus according to claim 13, wherein the hysteresis removing means calculates the corrected value of the self aligning torque with the hysteresis characteristic removed therefrom, using the estimated value of the self aligning torque, as the corrected value.

17. The physical amount estimating apparatus according to claim 16, wherein the corrected value of the self aligning torque is calculated by calculating equations, which each include a gradient represented by a ratio of a change in the corrected value of the self aligning torque to a change in the estimated value of the self aligning torque, and which equations are different for respective regions due to a gradient of a region, where the estimated value of the self aligning torque varies due to Coulomb friction, being made smaller than gradients of regions other than the region.

18. The physical amount estimating apparatus according to claim 1, further comprising:

a steering angle sensor for detecting a steering angle;

a vehicle speed sensor for detecting a vehicle speed;

a torque sensor for detecting a steering torque;

an assist torque sensor for detecting an assist torque of steering;

slip angle estimating means for estimating a slip angle of a steered wheel based on the steering angle and the vehicle speed;

self aligning torque estimating means for estimating a self aligning torque based on the steering torque and the assist torque;

hysteresis removing means for calculating a corrected value of the self aligning torque with a hysteresis characteristic removed therefrom, based on an estimated value of the self aligning torque; and air pressure reduction estimating means for estimating whether an air pressure of a tire is reduced, based on the corrected value of the self aligning torque and the slip angle.

19. The physical amount estimating apparatus according to claim 18, wherein the hysteresis removing means calculates the corrected value of the self aligning torque by calculating equations, which each include a gradient represented by a ratio of a change in the corrected value of the self aligning torque to a change in the estimated value of the self aligning torque, and which equations are different for respective regions due to a gradient of a region, where the estimated value of the self aligning torque varies due to Coulomb friction, being made smaller than gradients of regions other than the region.

20. The physical amount estimating apparatus according to claim 18, wherein the air pressure reduction estimating means estimates whether the air pressure of the tire is reduced, based on the corrected value of the self aligning torque and a reference value of the self aligning torque, which is set in accordance with the slip angle of the steered wheel, or based on a gradient of the corrected value of the self aligning torque, represented by a ratio of a change in the corrected value of the self aligning torque to a change in the slip angle.

21. The physical amount estimating apparatus according to claim 2, wherein the hysteresis removing means calculates the corrected value of the self aligning torque by calculating equations, which each include a gradient represented by a ratio of a change in the corrected value of the self aligning torque to a change in the estimated value of the self aligning torque, and which equations are different for respective regions due to a gradient of a region, where the estimated value of the self aligning torque varies due to Coulomb friction, being made smaller than gradients of regions other than the region.

22. The physical amount estimating apparatus according to claim 2, wherein the air pressure reduction estimating means estimates whether an air pressure of a tire is reduced, based on the corrected value of the self aligning torque and a reference value of the self aligning torque, which is set in accordance with the side force of the steered wheel, or based on a gradient of the corrected value of the self aligning torque, represented by a ratio of a change in the corrected value of the self aligning torque to a change in the side force.

* * * * *